US009414811B2

(12) United States Patent
Matsumoto et al.

(10) Patent No.: US 9,414,811 B2
(45) Date of Patent: Aug. 16, 2016

(54) ULTRASOUND DIAGNOSTIC DEVICE, IMAGE PROCESSING METHOD FOR ULTRASOUND DIAGNOSTIC DEVICE, AND NON-TRANSITORY COMPUTER-READABLE RECORDING MEDIUM

(71) Applicant: Konica Minolta, Inc., Tokyo (JP)

(72) Inventors: Yuki Matsumoto, Settsu (JP); Kazuya Takagi, Toyonaka (JP)

(73) Assignee: KONICA MINOLTA, INC., Tokyo (JP)

( * ) Notice: Subject to any disclaimer, the term of this patent is extended or adjusted under 35 U.S.C. 154(b) by 172 days.

(21) Appl. No.: 14/462,978

(22) Filed: Aug. 19, 2014

(65) Prior Publication Data

US 2015/0051488 A1 Feb. 19, 2015

(30) Foreign Application Priority Data

Aug. 19, 2013 (JP) ................... 2013-169527
Aug. 21, 2013 (JP) ................... 2013-171033
Aug. 6, 2014 (JP) ................... 2014-160638

(51) Int. Cl.
*A61B 8/14* (2006.01)
*A61B 8/08* (2006.01)
*G06T 7/00* (2006.01)
*A61B 8/06* (2006.01)
*A61B 8/00* (2006.01)

(52) U.S. Cl.
CPC .............. *A61B 8/5223* (2013.01); *A61B 8/0875* (2013.01); *G06T 7/0083* (2013.01); *A61B 8/06* (2013.01); *A61B 8/0858* (2013.01); *A61B 8/14* (2013.01); *A61B 8/463* (2013.01); *G06T 2207/10132* (2013.01); *G06T 2207/30008* (2013.01)

(58) Field of Classification Search
CPC ....... A61B 8/06; A61B 8/0858; A61B 8/0875; A61B 8/14; A61B 8/463; A61B 8/5223; G06T 2207/10132; G06T 2207/30008; G06T 7/0083

See application file for complete search history.

(56) References Cited

U.S. PATENT DOCUMENTS

2013/0060121 A1   3/2013   Patwardhan et al.

FOREIGN PATENT DOCUMENTS

JP   2013-056156 A   3/2013

OTHER PUBLICATIONS

Koike T.; The new concept of rheumatoid arthritis care—ultrasonography for joints; Medical Review Co., Ltd.; Mar. 2010; pp. 40-43.

*Primary Examiner* — Mark Remaly
(74) *Attorney, Agent, or Firm* — Lucas & Mercanti, LLP

(57) ABSTRACT

An ultrasound diagnostic device including a component specifier. Assume a first direction is a depth direction substantially perpendicular to a surface of a subject, a second direction is a direction orthogonal to the first direction, a first pixel is a pixel at a pixel location N in the second direction, a second pixel is a pixel at a pixel location N+1 in the second direction, and N is a positive integer. The component specifier detects one or more feature lines from the ultrasound image by repeatedly, while incrementing N, linking the first pixel with the second pixel when luminance of the second pixel is high and the second pixel is in close proximity to the first pixel, and specifies which of the one or more feature lines indicates a boundary between components, based on an order in the first direction of the one or more feature lines.

25 Claims, 21 Drawing Sheets

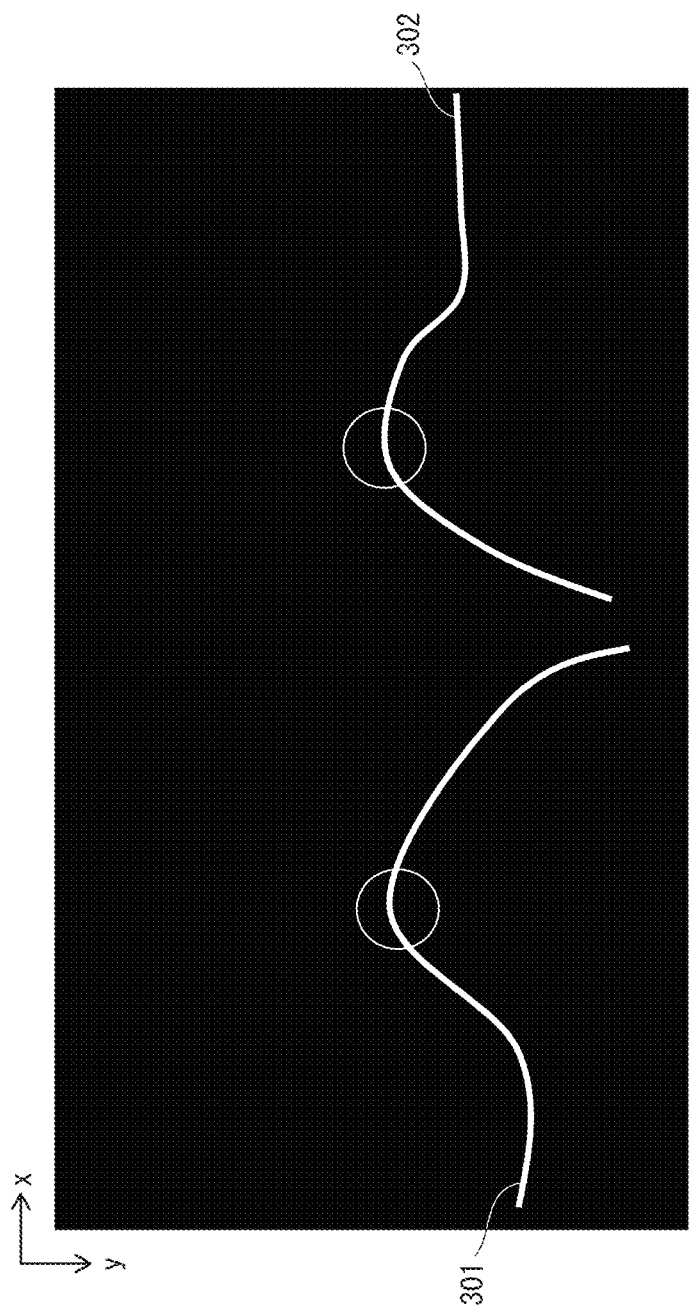

US 9,414,811 B2

ULTRASOUND DIAGNOSTIC DEVICE, IMAGE PROCESSING METHOD FOR ULTRASOUND DIAGNOSTIC DEVICE, AND NON-TRANSITORY COMPUTER-READABLE RECORDING MEDIUM

This application is based on an application No. 2013-169527 filed in Japan on Aug. 19, 2013, an application No. 2013-171033 filed in Japan on Aug. 21, 2013, and an application No. 2014-160638 filed in Japan on Aug. 6, 2014, the contents of which are hereby incorporated by reference.

BACKGROUND OF THE INVENTION (1) Field of the Invention

The present invention relates to ultrasound diagnostic devices, ultrasound image analysis methods, and programs thereof that are used to perform ultrasound diagnosis by bringing an ultrasound probe that performs transmission and reception of ultrasound waves into contact with a body surface, and in particular limb joints, of a subject.

(2) Description of the Related Art

In recent years the use of ultrasound diagnostic devices to evaluate disease activity of arthritis, including rheumatoid arthritis, is becoming common. In the evaluation of disease activity, B-mode images and power Doppler images are mainly used. Synovial thickening, synovial fluid retention, and bone erosion may be observed in B-mode images, and synovitis may be observed in power Doppler images.

In addition, methods have been proposed of using ultrasound images to grade disease activity of such conditions. In a case in which power Doppler images are used to grade synovitis levels, grades are determined depending on what proportion of a synovial membrane region that is thickened is occupied by a blood-flow signal that is observed.

In order to objectively quantify disease activity from ultrasound images, eliminating user activity, including subjectivity of the examiner, and quantifying according to certain criteria, is preferable. For example, Takao Koike, New treatment of rheumatoid arthritis using ultrasound investigation, Medical Review Co., Ltd., Mar. 10, 2010, pp. 40-43, proposes having an examiner trace freehand on an ultrasound image an articular cavity lined by a synovial membrane that is thickened, and calculating an occupation ratio of a blood-flow signal in the region traced as a quantitative evaluation value. However, by making the examiner trace the articular cavity in freehand, variations occur in the trace result because a trace of an articular cavity from the same ultrasound image may vary depending on the examiner, and even the same examiner may produce a different trace at different times. As a result, quantification of the occupation ratio of a blood-flow signal varies depending on subjectivity of the examiner.

In order to solve the above technical problem, in Japanese Patent Application Publication No. 2013-056156, for example, a method is proposed of objectively quantifying disease activity by analysis of an articular cavity region by clipping out an articular cavity region after specifying a bone surface. According to this method, subjectivity of the examiner is eliminated, and not only a blood-flow signal, but also image findings such as destruction of bone cortex, narrowing of a joint due to cartilage damage, extension of an articular capsule due to synovial thickening, etc., can be quantitatively evaluated.

SUMMARY OF THE INVENTION

Problems to be Solved by the Invention

However, in order to quantify disease activity with a higher level of objectivity, increasing detection accuracy of components of a joint such as bone surfaces, articular cavity region, etc., is important. Conventionally, detection of boundaries of such components uses edge detection technology by setting a threshold value for luminance and using a differential, second-order differential, etc., with respect to luminance in a direction that is substantially perpendicular to boundaries of components. However, in such a method, in locations where multiple components exist, such as joints, multiple boundaries are acquired as a single line drawing. Thus, to specify each component, pattern matching, etc., needs to be performed, and determination is necessary of which edge corresponds to which boundary of a component. Thus, an appropriate pattern does not always exist, causing situations in which components cannot be specified, boundaries of one component and another are falsely recognized, etc.

The present invention aims to provide an ultrasound diagnostic device that accurately specifies each component that makes up a joint.

Means for Solving the Problems

The ultrasound diagnostic device pertaining to an aspect of the present invention is an ultrasound diagnostic device that specifies, from an ultrasound image of a subject that includes a joint, a joint image portion that indicates components of the joint, the ultrasound diagnostic device comprising: an image processing circuit that acquires the ultrasound image and specifies the joint image portion, including: an ultrasound image acquirer that acquires the ultrasound image; and a component specifier that specifies an image portion indicating a boundary between the components, wherein when a first direction is a depth direction substantially perpendicular to a surface of the subject, a second direction is a direction orthogonal to the first direction, a first pixel is a pixel at a pixel location N in the second direction, a second pixel is a pixel at a pixel location N+1 in the second direction, and N is a positive integer, the component specifier detects one or more feature lines from the ultrasound image by repeatedly, while incrementing N, linking the first pixel with the second pixel when luminance of the second pixel is high and the second pixel is in close proximity to the first pixel, and specifies which of the one or more feature lines indicates a boundary between the components, based on an order in the first direction of the one or more feature lines.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIG. 11 illustrates an edge of an edge of a bone surface in an ultrasound image;

DESCRIPTION OF THE PREFERRED EMBODIMENT

The following is a description of an embodiment of the present invention with reference to the drawings.

Embodiment

Figure 1:
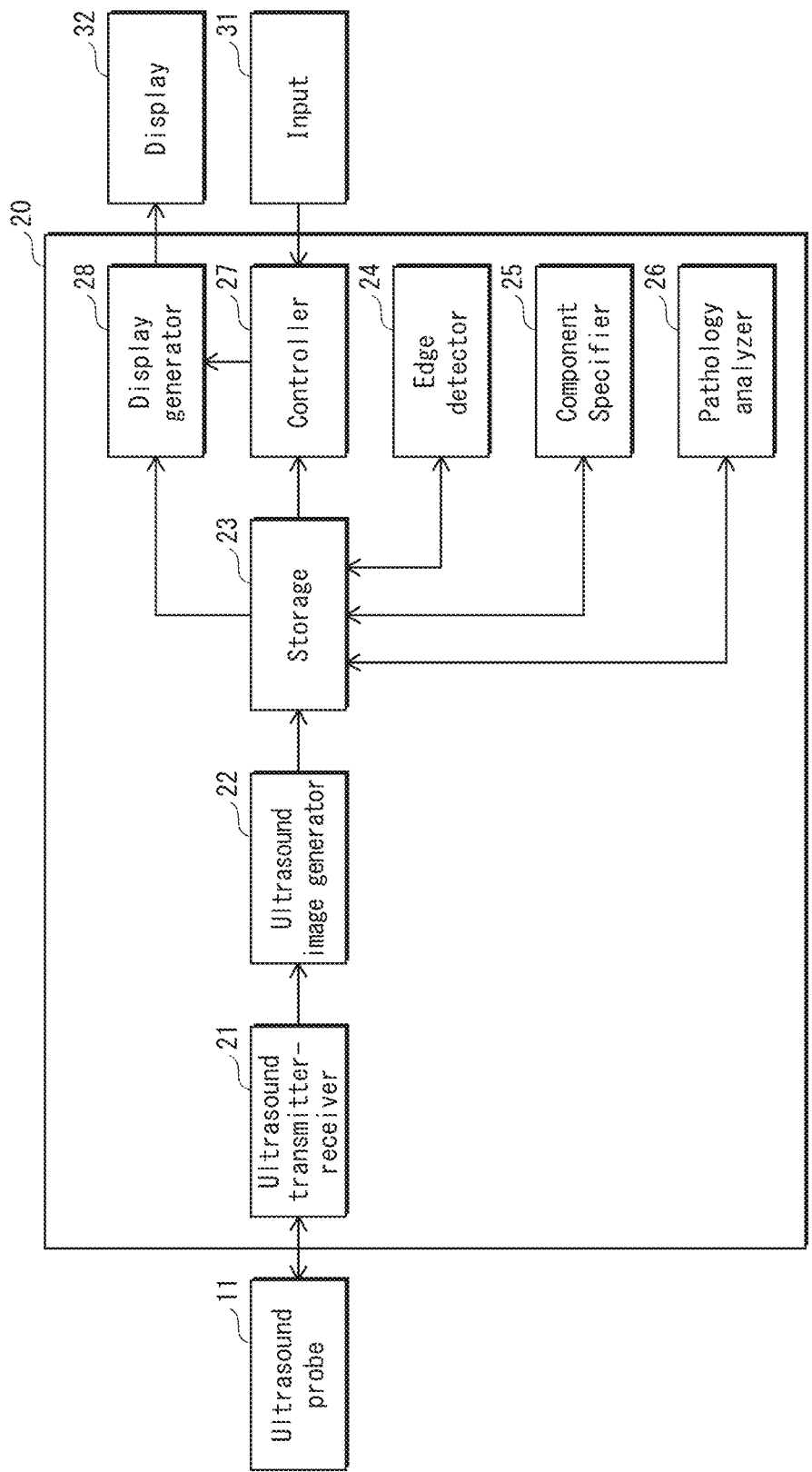
FIG. 1 is a block diagram of an ultrasound diagnostic device pertaining to an embodiment.

FIG. 1 is a block diagram illustrating a configuration of an ultrasound diagnostic device pertaining to the embodiment. An ultrasound diagnostic device 20 includes an ultrasound transmitter-receiver 21, an ultrasound image generator 22, a storage 23, an edge detector 24, a component specifier 25, a pathology analyzer 26, a controller 27, and an display generator 28. The ultrasound image generator 22, the storage 23, the edge detector 24, and the component specifier 25 compose an image processing circuit and are configured as one circuit. Note that the ultrasound transmitter-receiver 21, the pathology analyzer 26, the controller 27, and the display generator 28 are configured as one or more circuits different from the image processing circuit. Alternatively, the ultrasound transmitter-receiver 21, the pathology analyzer 26, the controller 27, and the display generator 28 may be configured as part of the image processing circuit if required. An ultrasound probe 11, an input 31, and a display 32 are externally connected to the ultrasound diagnostic device 20. Alternatively, the ultrasound probe 11, the input 31, and the display 32 may be included in the ultrasound diagnostic device 20.

The ultrasound probe 11 is, for example, a linear probe including a row of transducers that include lead zirconate titanate (PZT), etc., arranged as a transducer array. The ultrasound probe 11 converts an ultrasound transmission signal generated by the ultrasound transmitter-receiver 21 to a transmit ultrasound wave, and transmits the ultrasound wave to a subject. The transmitted transmit ultrasound wave is reflected at a position within the subject, i.e., a living organism, where a difference in acoustic impedance exists between components of a joint. The greater the difference in acoustic impedance, the greater the energy of the ultrasound wave that is reflected.

A reflected ultrasound wave is received by the ultrasound probe 11. The ultrasound wave received by the ultrasound probe 11 is inputted to the ultrasound transmitter-receiver 21 as an ultrasound reception signal. The ultrasound transmitter-receiver 21 performs beamforming by delay-and-sum, and outputs an ultrasound reception signal after delay-and-sum as an echo signal in scan lines pertaining to one transmission and reception of an ultrasound wave.

The ultrasound image generator 22 aggregates echo signals inputted from the ultrasound transmitter-receiver 21, performs envelope detection, logarithmic compression, etc., and changes the echo signals to luminance data. In addition to this, the ultrasound image generator changes a position of a scan line and depth in the scan line to orthogonal coordinates, and generates an ultrasound image. The ultrasound image generated by the ultrasound image generator 22 is temporarily stored at the storage 23.

The storage 23 is a storage device that temporarily stores an ultrasound image, specification information and disease activity of components (described later), and may include, for example, RAM, flash memory, a hard disk drive, etc.

The input 31 is a configuration for the examiner to input an examiner name, a patient name, and setting information of the ultrasound diagnostic device, and, for example, may include an input device such as a keyboard, trackball, pen tablet, etc. Further, for example, the input 31 may be integrated with the display 32 (described later) as a touch panel, etc.

The edge detector 24 reads an ultrasound image stored by the storage 23 and detects an edge in the ultrasound image. An edge that is detected is used for specifying an image portion that indicates a component of a joint (hereafter referred to as "component") from an ultrasound image.

The component specifier 25 specifies each component in an ultrasound image, by using an edge detected by the edge detector 24. Specifically, from an ultrasound image of a joint, the component specifier 25 specifies image portions each indicating a bone surface, a joint position, an articular cavity region, and a synovial membrane (hereafter referred to as "bone surface", "joint position", "articular cavity region", and "synovial membrane", respectively).

The pathology analyzer 26 analyzes each component of an ultrasound image specified by the component specifier 25, and quantitatively evaluates disease activity of a pathology of rheumatoid arthritis.

The controller 27 holds setting information inputted by a user via the input 31 in association with an ultrasound image stored by the storage 23. Further, the controller 27 acquires each component of an ultrasound image specified by the component specifier 25 and an evaluation result of disease activity output by the pathology analyzer 26, and notifies the display generator 28 of such data along with setting information.

The display generator 28 reads an ultrasound image stored by the storage 23. Further, the display generator 28 receives from the controller 27 an examiner name, patient name, time information, and setting information of the ultrasound diagnostic device inputted from the input 31, and an evaluation result of disease activity output by the pathology analyzer 26. The display generator 28 superimposes such information on the ultrasound image, and outputs to the display 32.

The display 32 is a monitor that displays an image generated by the display generator 28 to an examiner, and is, for example, an LCD display.

The ultrasound transmitter-receiver 21, the ultrasound image generator 22, the edge detector 24, the component specifier 25, the pathology analyzer 26, the controller 27, and the display generator 28 are each implemented, for example, by memory, a programmable device such as a central processing unit (CPU) or a graphic processing unit (GPU), and software or hardware such as a field programmable gate array (FPGA), an application specific integrated circuit (ASIC), etc.

<Measurement Target>

Figure 2:
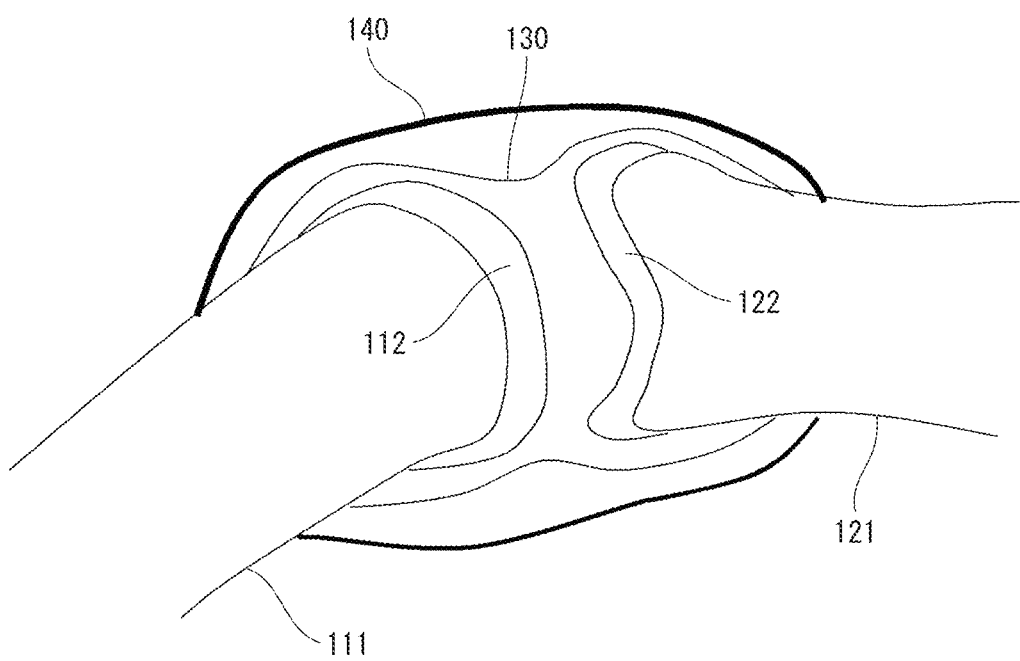
FIG. 2 illustrates an outline of a joint.

The main target when measuring a subject in the present embodiment is a joint. As an example of a joint, a schematic of a finger joint is illustrated in FIG. 2. As illustrated in FIG. 2, the joint includes a bone 11, a bone 121, cartilage 112, cartilage 122, a synovial membrane 130, and an articular capsule 140. The cartilage 112 and the cartilage 122 are incidental to a tip portion of the bone 111 and the bone 121, respectively, and the synovial membrane 130 exists so as to enclose the cartilage 112 and the cartilage 122. The articular capsule 140 is attached to the bone 111 and the bone 121 so as to surround the synovial membrane 130.

For example, as rheumatoid arthritis progresses, thickening of the synovial membrane 130, accumulation of synovial fluid in the synovial membrane 130, and bone erosion due to destruction of bone cortex may be confirmed. Further, due to destruction of the cartilage 112 and the cartilage 122, gaps in the joint may become narrow and the joint may ankylose. Further, in many cases, an increase in angiogenesis in the synovial membrane is observed.

Using FIG. 3A and FIG. 3B, ultrasound image of joints and pathology of rheumatoid arthritis is described below.

Figure 3A:
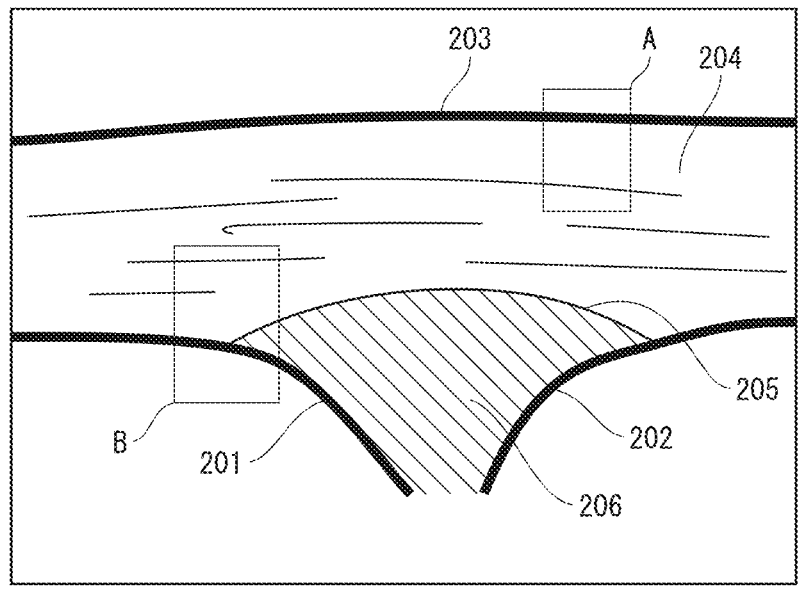
FIG. 3A illustrates an example of an ultrasound image of a joint.

FIG. 3A is an ultrasound image of a joint that is not suffering from rheumatoid arthritis. In the ultrasound image, a bone surface 201, a bone surface 202, skin 203, sinew 204, and an articular capsule 205 are illustrated. The bone surface 201, the bone surface 202, and the skin 203 are comparatively hard components, and are therefore illustrated in the ultrasound image at a high luminance A region surrounded by the bone surface 201, the bone surface 202, and the articular capsule 205 is an articular cavity region 206.

A majority of ultrasound waves that reach the bone 111 and the bone 112 are reflected at bone surfaces, and therefore an interior of the bones are not illustrated, and only the bone surfaces are illustrated having high luminance. The sinew 204 and the articular capsule 205 are illustrated having a low luminance compared to the bone surface 201, the bone surface 202, and the skin 203. Further, the synovial membrane 130 has an even lower luminance than the sinew 204 and the articular capsule 205, and the cartilage 112 and the cartilage 122 have almost no luminance. Accordingly, in an ultrasound image of the joint, in addition to the skin 203, the bone surface 201, and the bone surface 202, the sinew 204 and the articular capsule 205 are illustrated having a comparatively high luminance.

Figure 3B:
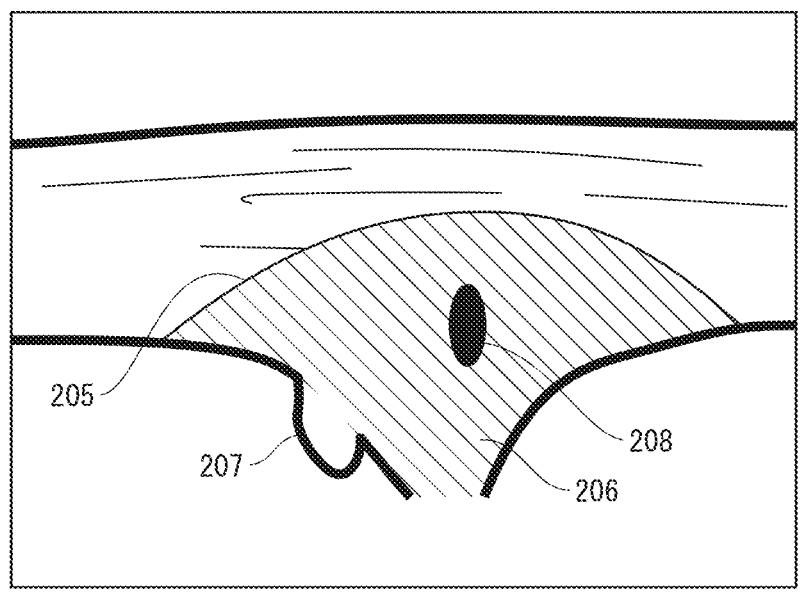
FIG. 3B illustrates an example of an ultrasound image of a joint suffering from rheumatoid arthritis.

On the other hand, FIG. 3B is an ultrasound image of a joint that is suffering from rheumatoid arthritis. As disease activity of rheumatoid arthritis progresses, the synovial membrane 130 gets thicker, and therefore the articular capsule 140 that surrounds the synovial membrane 130 also enlarges. Thus, in the ultrasound image enlargement of the articular capsule 205 is observed. Further, destruction of bone cortex is observed in the ultrasound image as bone erosion 207. Furthermore, inside the articular cavity region 206, a blood-flow signal 208 that is attributable to angiogenesis is observed.

<Operations>

Figure 4:
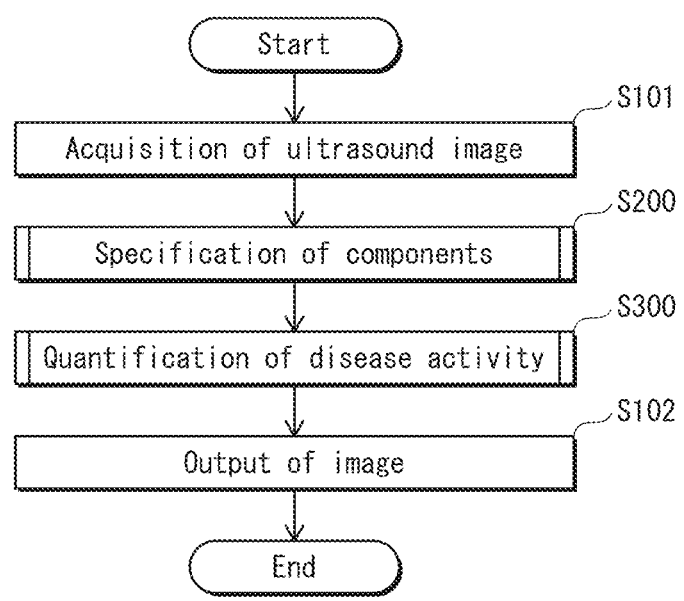
FIG. 4 is a flowchart illustrating an operation of the ultrasound diagnostic device pertaining to the embodiment.

Operations of the ultrasound diagnostic device 20 pertaining to the embodiment are described below. FIG. 4 is a flowchart illustrating an overall operation of the ultrasound diagnostic device 20.

First, an ultrasound image is acquired (step S101). Specifically, the ultrasound transmitter-receiver 21 transmits an ultrasound transmission signal to the ultrasound probe 11, and the ultrasound probe 11 changes the ultrasound transmission signal to a transmit ultrasound wave and transmits the transmit ultrasound wave to the subject. The ultrasound probe 11 changes a reflected ultrasound wave that is reflected from the subject to an ultrasound reception signal and transmits the ultrasound reception signal to the ultrasound transmitter-receiver 21. The ultrasound transmitter-receiver 21 performs beamforming by delay-and-sum with respect to the ultrasound reception signal, and outputs an echo signal to the ultrasound image generator 22. The ultrasound image generator 22 performs envelope detection, logarithmic compression, etc., with respect to the echo signal, and changes the echo signal to luminance data. In addition to this, the ultrasound image generator 22 changes a position of a scan line and depth in the scan line to orthogonal coordinates, and generates an ultrasound image. The following assumes the ultrasound image is a B-mode image, but the ultrasound image is not limited to being a B-mode image, and may be any image generated using ultrasound waves, such as an M-mode image, a power Doppler image, etc. The ultrasound image generated by the ultrasound image generator 22 is stored at the storage 23.

Next, components are specified from the ultrasound image (step S200). By this operation, a bone surface and a synovial membrane are specified, and from the bone surface and the synovial membrane, a bone end, joint position, articular capsule, and articular cavity region are specified. Information of each component so specified is stored at the storage 23. Details are described later.

Next, disease activity is quantified (step S300). Disease activity is an indicator that indicates, with respect to joint diseases such as rheumatoid arthritis, presence or absence of disease, and in the presence of disease, the progress thereof. For example, a degree of thickening of a synovial membrane and articular capsule, smoothness of a bone surface, a shape of a joint, presence or absence of blood flow in an articular cavity region and in the presence of blood flow, a range of blood flow in the articular cavity region, etc. By quantifying disease activity, judgment of presence, absence, and degree of progress of a joint disease, and objective evaluation of progress of a joint disease over a predetermined period, etc., are possible, and precise care, etc., can be performed with respect to a subject. According to this operation, disease activity of rheumatoid arthritis in each of a bone surface, synovial membrane, joint, articular capsule, and articular cavity region is quantified. A result of quantification of disease activity in each of such components is stored at the storage 23. Details are described later.

Finally, an image is generated and outputted to the display 32 (step S102). Specifically, an examiner name, patient name, time information, and setting information of the ultrasound diagnostic device from the input 31, and evaluation result of disease activity output by the pathology analyzer 26 are superimposed on an ultrasound image stored by the storage 23, and outputted to the display 32.

<Component Specification>

Figure 5:
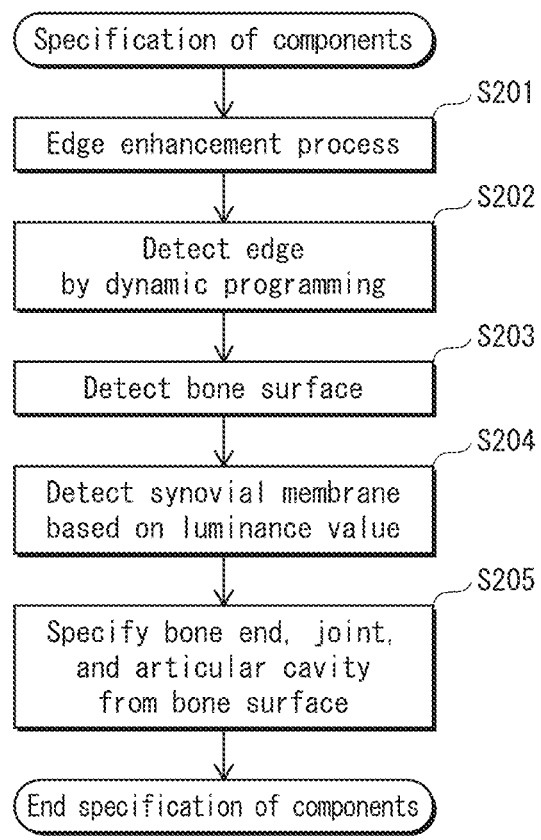
FIG. 5 is a flowchart illustrating a component specification operation of the ultrasound diagnostic device pertaining to the embodiment.

Component specification in step S200 is described in detail below. FIG. 5 is a flowchart illustrating a component specification operation.

Note that in the present embodiment, in an ultrasound image, a depth direction is a y axis, and a direction orthogonal to the y axis, or in other words a direction approximately parallel to skin, is an x axis. Further, the upper-left of an ultrasound image is an origin, coordinate values on the x axis increase from left to right, and coordinate values on the y axis increase from top to bottom. In other words, a side near the skin is up and a side farther from the skin is down. In the following, a deep side is referred to as down and a shallow side is referred to as up, but this indicates the same relationship as described above.

Figure 6A:
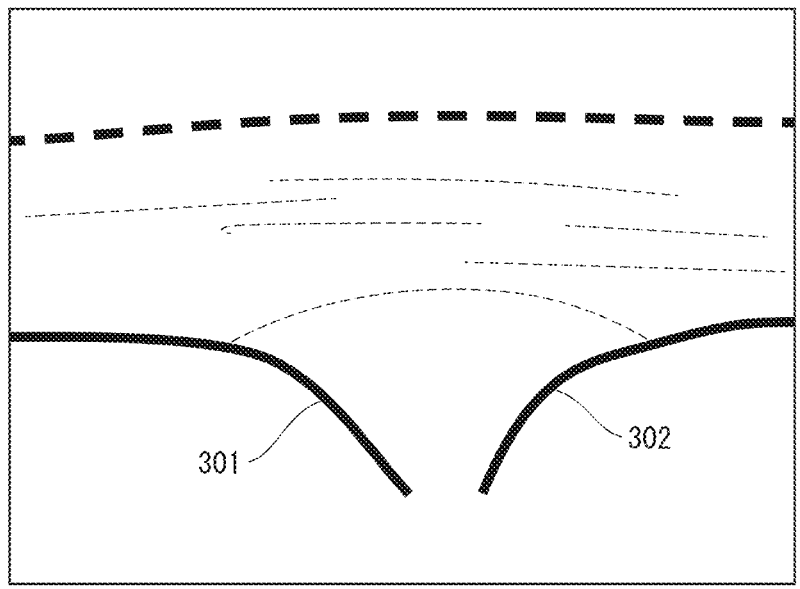
FIG. 6A illustrates a bone surface in an ultrasound image of a joint.

As mentioned above, energy of a reflected ultrasound wave increases corresponding with an increase in difference of acoustic impedance between components in a subject. Accordingly, it is likely that a linear region that has a high luminance in an ultrasound image indicates a component boundary. Further, as mentioned above, a bone surface is depicted with high luminance, and a region deeper than a bone surface (bone interior) has almost no luminance. Thus, after detecting a potential boundaries of components, first specifying a bone surface, then specifying boundaries of other components at shallower depths, is efficient. FIG. 6A illustrates linear areas of high luminance detected from an image of a joint region. Specification is performed starting from a bone surface 301 and a bone surface 302. Note that in FIG. 6A, edges other than the bone surface 301 and the bone surface 302 are indicated by dashed lines.

First, the edge detector 24 performs an edge enhancement process (step S201). Specifically, edges are extracted from the ultrasound image, here a B-mode image, and images of edges that are extracted and the source B-mode image are combined. In this way, even if the extraction of edges in the edge enhancement is performed imperfectly, such that one component boundary is extracted as two independent edges, etc., the source B-mode image compensates for this, and therefore a corresponding edge (feature line) detected in edge detection (described later) is not broken. Here, edge enhancement may be performed through: the Sobel filter; a second derivative process; binary processing using a pre-set representative luminance value of a bone surface or a value inputted via the input 31 by an examiner as a threshold; a method of picking out a stressed edge from a differential image using the Sobel operator, Laplacian filter, etc.; a method of using the Canny algorithm to extract continuous edges; etc. For example, in a case of creating a first-order differential image using the Sobel operator, edges having intensity in a horizontal direction in an ultrasound image are emphasized by setting a derivative of the operator as shown by $L_y$ in the following formula (Math 1). $L_y$ in the following formula (Math 1) is a derivative for emphasizing luminance change in a direction from top to bottom in an image, and can extract edges that extend in a horizontal direction of the image.

$$L_y = \begin{bmatrix} +1 & +2 & +1 \\ 0 & 0 & 0 \\ -1 & -2 & -1 \end{bmatrix} \quad \text{[Math 1]}$$

Figure 7:
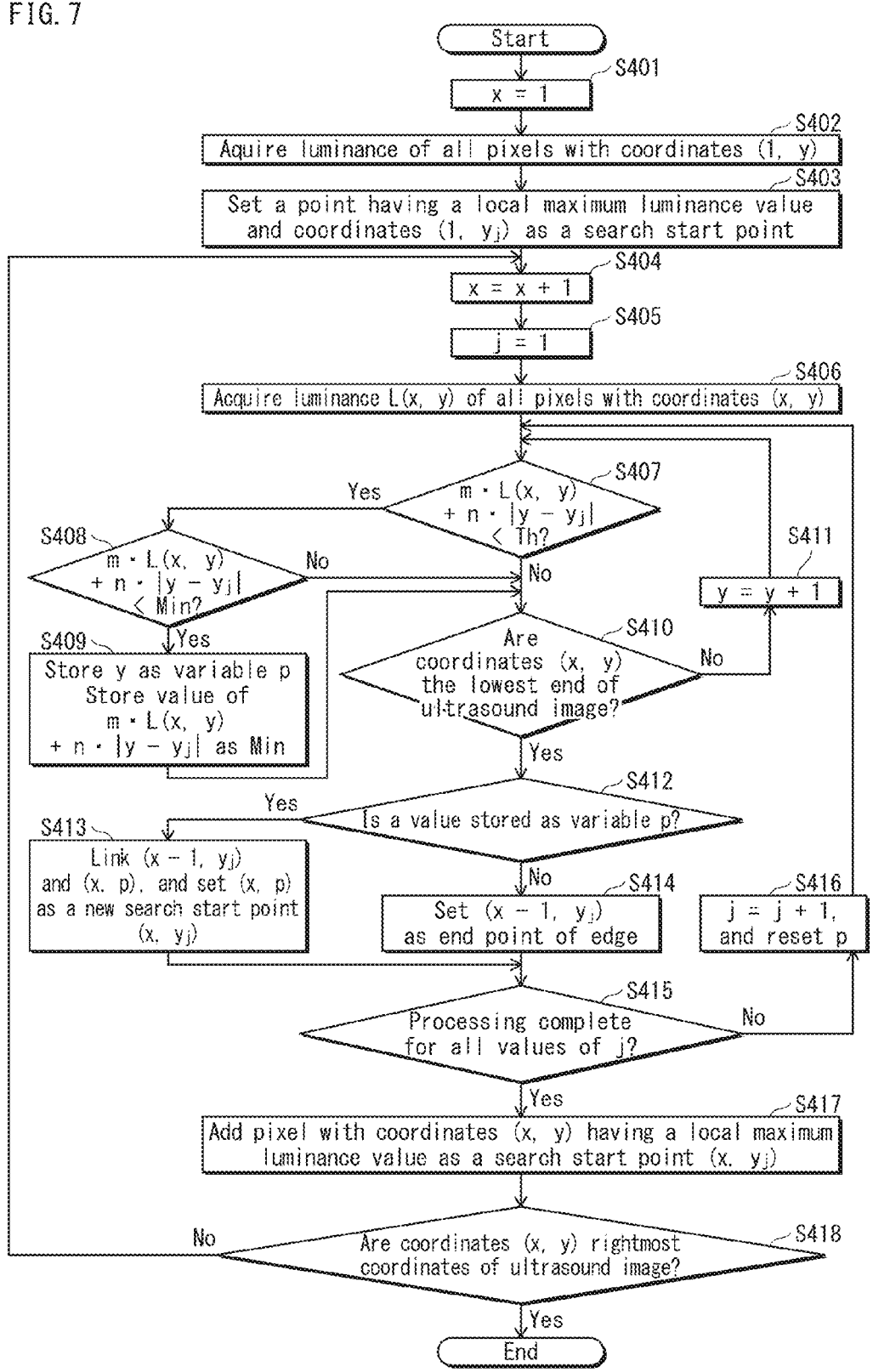
FIG. 7 is a flowchart illustrating an edge detection operation using dynamic programming pertaining to the embodiment.

Next, the edge detector 24 detects edges by dynamic programming (step S202). Here, in a target joint, each edge to be detected is a feature line indicating either a boundary line of a component or a fiber of fibrous tissue, and, unlike the edges extracted by the edge enhancement process as mentioned above, the edges detected here are not limited to those corresponding to areas having the highest luminescence. Details of the operation are illustrated in the flowchart of FIG. 7.

First, the edge detector 24 sets x as one (step S401) and acquires luminance values for every pixel with an x coordinate of one (step S402). Next, with respect to the acquired luminance values, the edge detector 24 picks out and stores pixels having a local maximum luminance value (peak) in the y axis direction as search start points (step S403). In the following, each of j search start points (j is a positive integer) is denoted as a coordinate $(1, y_j)$ Next, for each search start point, the edge detector 24 searches for a pixel that makes up a same edge with the search start point. Specifically, the edge detector 24 increments the x coordinate by one (step S404) and, for each search start point, performs a search of a corresponding point from among pixels with an x coordinate of two. Specifically, the edge detector 24 acquires luminance values for every pixel with an x coordinate of two (step 406). Then, based on Math 2 below, searches for a pixel having a minimum Value ("Value" indicating the value defined in Math 2) among all pixels with an x coordinate of two.

$$\text{Value}=m \cdot L(x,y)+n \cdot |y-y_j| \quad \text{[Math 2]}$$

Here, $L(x, y)$ is a luminance value of a pixel with a coordinate $(x, y)$. Further, m and n satisfy the relationship n>0>m.

Specifically, first the edge detector 24 determines whether or not the Value is below a threshold value Th (step S407). This determination is made because when $|y-y_j|$ is very large, or in other words the difference in y coordinates of the search start point and the given pixel is large, the search start point and the given pixel do not make up the same continuous edge. Note that this determination, instead of whether or not the Value is below the threshold value Th, may be performed based on whether or not $|y-y_j|$ is below a predetermined threshold value. Next, the edge detector 24 determines, from among pixels having a Value below the predetermined threshold value Th, a pixel with a minimum Value. Specifically, the edge detector 24 determines whether a Value for a given pixel is below a minimum value Min (step S408), and when the Value is below the minimum value Min, the y coordinate of the given pixel is stored in a variable p, and the Value is set as the new minimum value Min (step S409). Note that an initial value of the minimum value Min may be equal to the threshold value Th, or in a case in which the minimum value Min is not yet defined, the initial value of the minimum value Min may be defined upon a "Yes" determination at step S408.

The processing of steps S407-S409 is executed with respect to all pixels with an x coordinate of two. That is, the edge detector 24 repeats such processing while incrementing y by one each time (step S411) until determining that the coordinates (2, y) reach the bottom of the ultrasound image (step S410).

In this way, in a case in which one or more pixels have a Value below the predetermined threshold Th ("Yes" at step S407), a y coordinate of a pixel that has the smallest Value is stored as the variable p and the Value for the pixel is stored as the minimum value Min. Accordingly, when a value is stored as the variable p ("Yes" at step S412), with respect to a search start point $(1, y_j)$, (x, p) is associated with $(1, y_j)$ as the next point in the same edge, and (x, p) is set as a new search start point (step S413). On the other hand, when no pixel exists having a Value below the predetermined value Th ("Yes" at step S407 does not occur), no value is stored as the variable p ("No" at step S412). In such a case, an edge is determined to end at $(x-1, y_j)$ (step S414).

By repeating the processing of steps S407-S414 with respect to every search start point (steps S415, S416), for every search start point with an x coordinate x−1 (e.g. one), when a corresponding point exists, the corresponding point is set as a new search start point, and when there is no corresponding point, the corresponding edge is determined to end. Note that in a case in which a single corresponding point with an x coordinate x (e.g. two) corresponds to a plurality of search start points, each with an x coordinate x−1 (e.g. one), for every combination other than the combination having the smallest Value, the corresponding point with an x coordinate x (e.g. two) may be considered an end of an edge, or each combination other than the combination having the smallest Value may be invalidated and another corresponding point may be searched for.

Next, the edge detector 24 acquires luminance values for every pixel with an x coordinate of two, picks out a pixel whose y coordinate is a local maximum luminance value, and adds the coordinates of such a pixel as a search start point (x, $y_j$) (step S417). At this time, a point already specified as a new search start point in step S413 is not added, to avoid duplication. In this way, (i) each corresponding point (x−1, $y_j$) specified in step S413, and (ii) a point whose y coordinate has a local maximum luminance value that is not included in the corresponding points specified in step S413, are set as new search start points.

The processing of steps S404-S417 is repeated with respect to the new search start points (step S418). In this way, the edge detector 24 detects whether or not, for each search start point with x=2, a corresponding point with x=3 exists, and sets one or more search start points with x=3. By repeating the above processing until a right-side end of the image is reached, an edge that is substantially parallel with the y axis is detected by a method that is efficient and has a low incidence of misidentification. For example, misidentification of high luminance noise that overlaps an edge as an edge is avoided, and misidentification of an edge that is interrupted near a center of an ultrasound image and a different edge that is not as deep as the interrupted edge as a single edge is avoided. By repeating this processing, a boundary of a component that is thought to be a bone surface is detected, for example, as illustrated in FIG. 8A.

Figure 8:
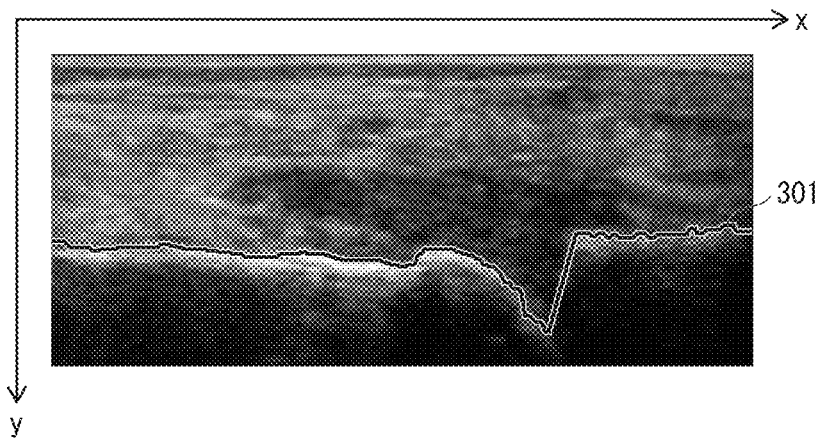
FIG. 8A illustrates an edge detected in an ultrasound image of a joint.
FIG. 8B illustrates an example of edge detection using dynamic programming pertaining to the embodiment.
FIG. 8C illustrates an example of values ("Value") in edge detection using dynamic programming pertaining to the embodiment.
FIG. 8D illustrates an example of edge detection using dynamic programming pertaining to the embodiment.
FIG. 8E illustrates an example of values ("Value") in edge detection using dynamic programming pertaining to the embodiment.

FIG. 8B and FIG. 8D illustrate a relationship between luminance values of pixels and a detected edge. FIG. 8B illustrates a relationship between a region A in FIG. 3 and luminance values of each pixel, and FIG. 8D illustrates a relationship between a region B in FIG. 3 and luminance values of each pixel. Note that here, m=−1, n=20, and Th=−20. In FIG. 8B, an edge 501 and an edge 502 are detected. If local maximum luminance values were simply detected following the y axis, when x=4, (4, 1) and (4, 2) would be detected, and there would be a possibility of misidentification of (4, 1) being linked to (3, 2) and (4, 2) being linked to (3, 6). However, in the method pertaining to the present embodiment, a difference in y coordinates is taken into account, and (4, 2) in the edge 501 is not misidentified as a part of the edge 502. FIG. 8C illustrates Values when (3, 6) is a search start point. The Value of (4, 2) is −20, and the Value of (4, 6) is −70, and therefore (3, 6) and (4, 6) are linked, whereas (3, 6) and (4, 2) are not linked.

Further, in FIG. 8D, edges 503-506 are detected. Here, as in FIG. 8B, pixels (5, 2), (5, 10), etc. are not misidentified as belonging to the edge 504. Thus, the edge 504 is correctly detected. FIG. 8E illustrates Values when (4, 6) is a search start point. In this case, since all Values are greater than or equal to the threshold value Th (−20), the search start point (4, 6) does not have a corresponding point. Thus, interruption of the edge 504 at (4, 6) is correctly recognized, and a situation where the edge 504 is connected with the edge 503 or the edge 506 does not occur. Further, since only one corresponding point is linked with each search start point, the edges 505 and 506, which are separate edges, are not misidentified as branch portions of a single edge. Since the Value for (5, 12) with respect to (4, 12) is −70, a part of the edge 505 that has a lower luminance (from (4, 12) to (5, 12)) is not missed from detection. Thus, the edges 505 and 506 are correctly identified, such that the edge 505 is an edge in close proximity to the edge 506.

Figure 6B:
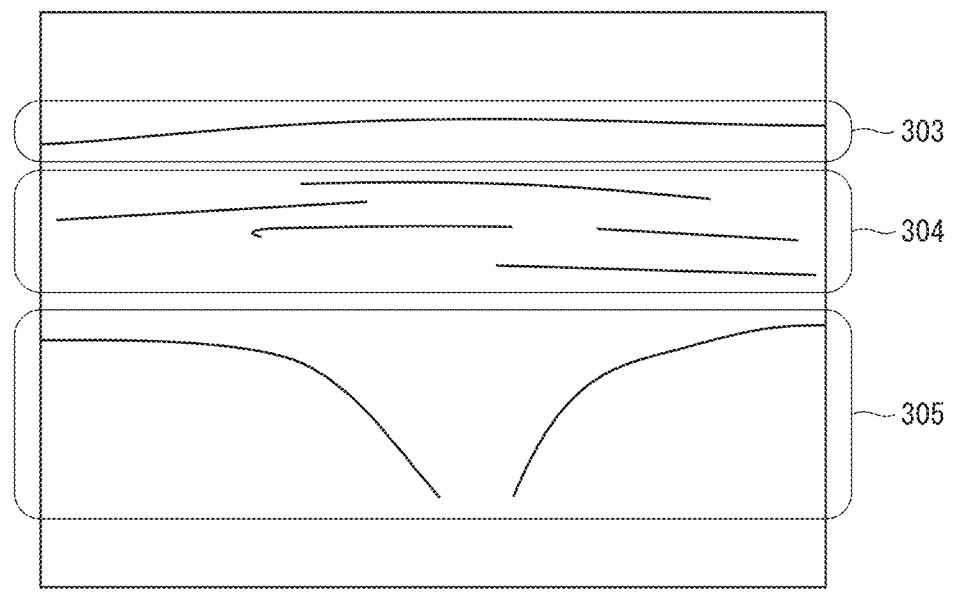
FIG. 6B illustrates edge classification in an ultrasound image of a joint.

Returning to FIG. 5, description continues. Next, a bone surface is detected by the component specifier classifying detected edges (step S203). FIG. 6B illustrates detected edges classified as a skin segment 303, a sinew segment 304, and a bone segment 305. Anatomically, the least deep position is skin, the deepest position is a bone surface, and between these is sinew and an articular capsule. Therefore, for example, by methods such as k-means clustering, mean-shift clustering, etc., that classify edges in proximity with each other on the image to one segment, edges detected in step S202 are classified to segments. In this way, edges included in the bone segment 305 are detected as bone surfaces.

Figure 9:
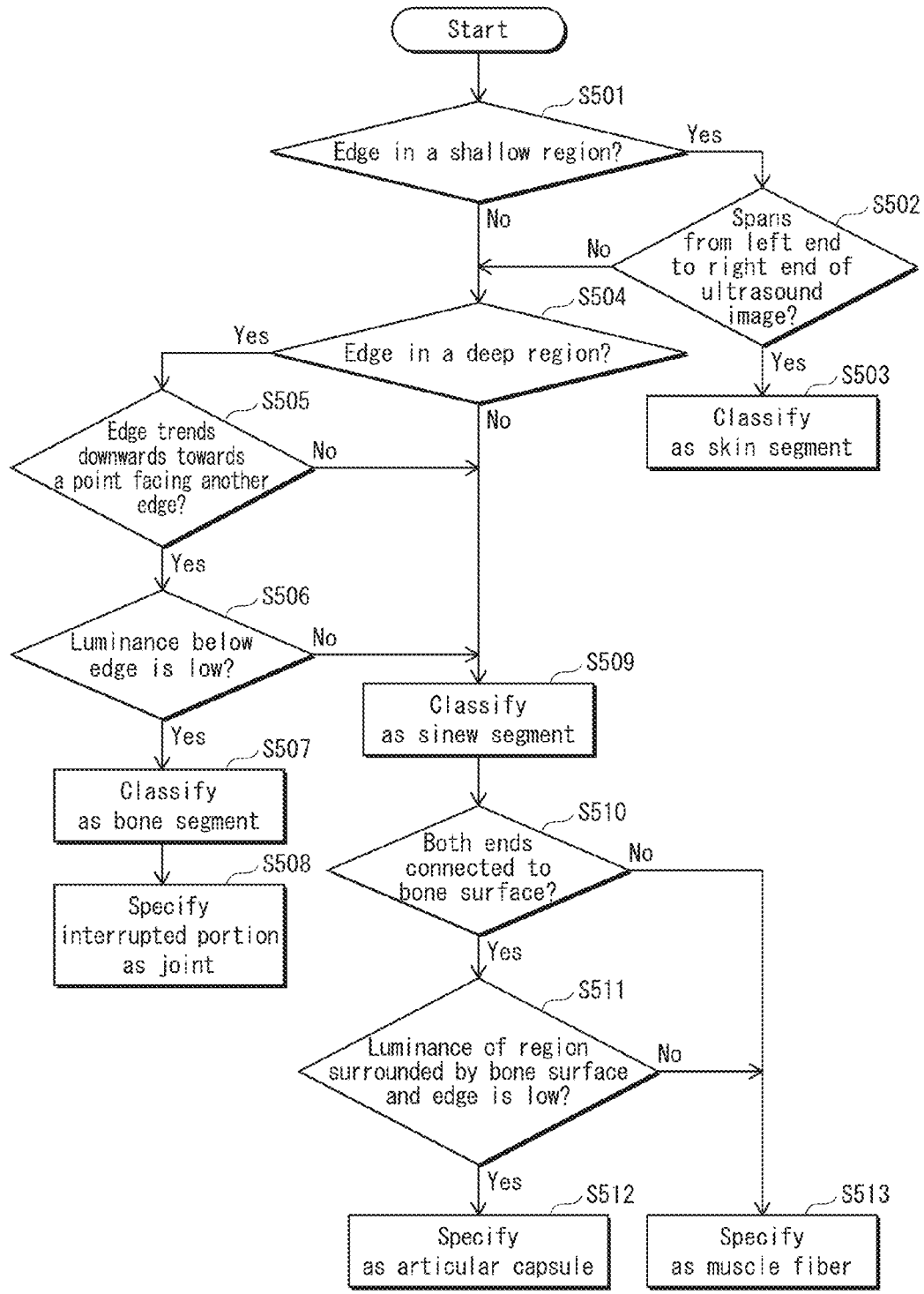
FIG. 9 is a flowchart illustrating an edge classification operation pertaining to the embodiment.

Specifically, an operation is performed such as the operation illustrated by the flowchart in FIG. 9. First, if an edge is in a shallow region (step S501), whether or not the edge spans from a left end to a right end of an ultrasound image is determined (step S502). A positive determination results in classification of the edge as belonging to a skin segment (step S503). Alternatively, if an edge is in a deep region (step S504), whether or not the edge trends downwards towards a point facing another edge (step S505) and whether or not luminance below the edges is low (step S506) is determined Positive determination for both steps results in classification of the edge as belonging to a bone segment (step S507). Alternatively, an edge that lies between the deep region and the shallow region, an edge in the shallow region that is not classified as belonging to a skin segment, and an edge in the deep region that is not classified as belonging to a bone segment are classified as belonging to a sinew segment (step S509).

In this way, boundaries of components of a joint are accurately detected as edges, and such edges are classified as either a bone surface, skin, articular capsule, muscle fiber, or sinew.

<Specification of Other Components>

Figure 10A:
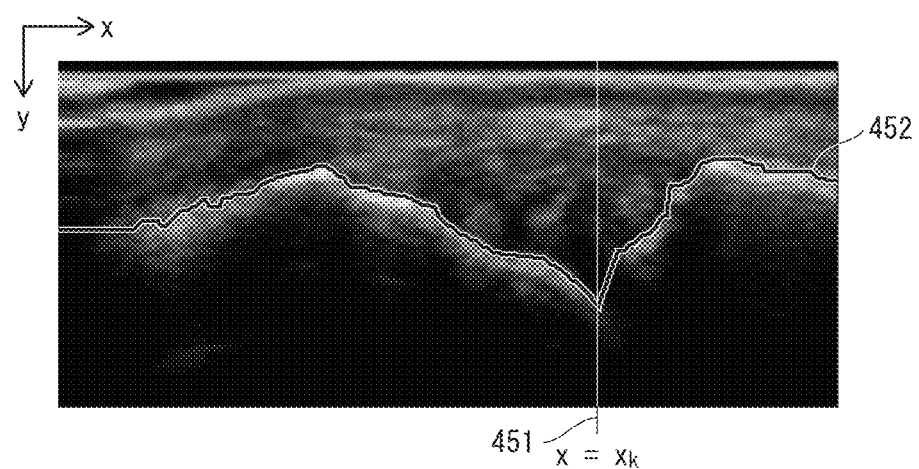
FIG. 10A illustrates an example of specification of a synovial membrane pertaining to the embodiment.
Figure 10B:
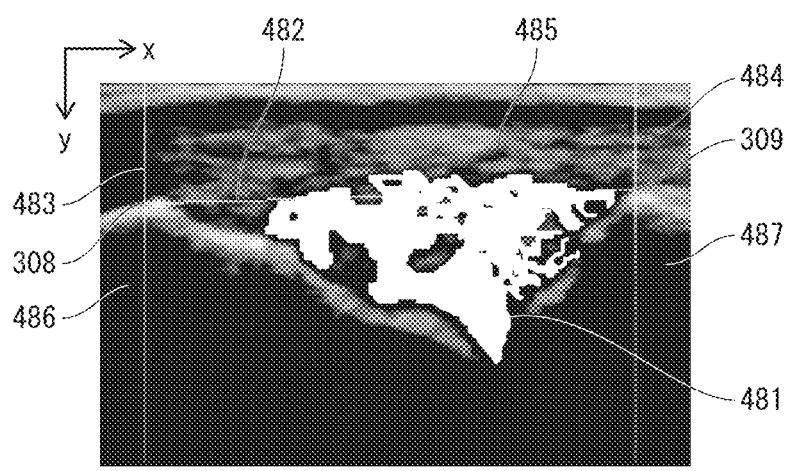
FIG. 10B illustrates an example of specification of a synovial membrane pertaining to the embodiment.

Returning to FIG. 5, description continues. Next, the component specifier 25 detects a synovial membrane based on luminance value (step S204). FIG. 10A and FIG. 10B illustrate a synovial membrane detection process. An edge 452 in FIG. 10A is a detected bone surface. The component specifier 25, for each x coordinate, acquires luminance values for each pixel from a top end of the ultrasound image to the bone surface, and detects whether or not the luminance values indicate a synovial membrane. For example, pixels on a straight line 451 of x=$x_k$ are classified as sinew or muscle fiber, or a synovial membrane. Specifically, based on two points: (i) synovial membrane is located deeper than muscle fiber, etc., and (ii) synovial membrane has a lower luminance than muscle fiber, etc., a pixel is classified as belonging to one of the two groups according to luminance value and depth. By performing the above processing for every x coordinate, a region in which synovial membrane exists is detected. FIG. 10B illustrates a synovial membrane region 481 detected in the ultrasound image.

Returning to FIG. 5, description continues. Next, based on the bone surface, a joint, bone ends, and articular cavity region are specified (step S204). The following describes how each of such components are detected.

Figure 12A:
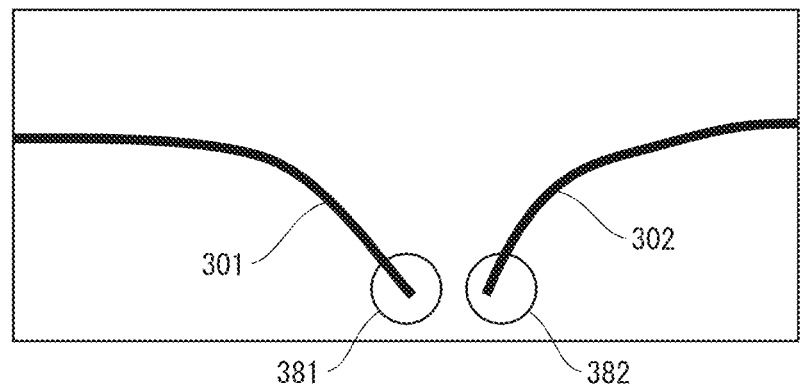
FIG. 12A illustrates an example of specification of a joint pertaining to the embodiment.
Figure 12B:
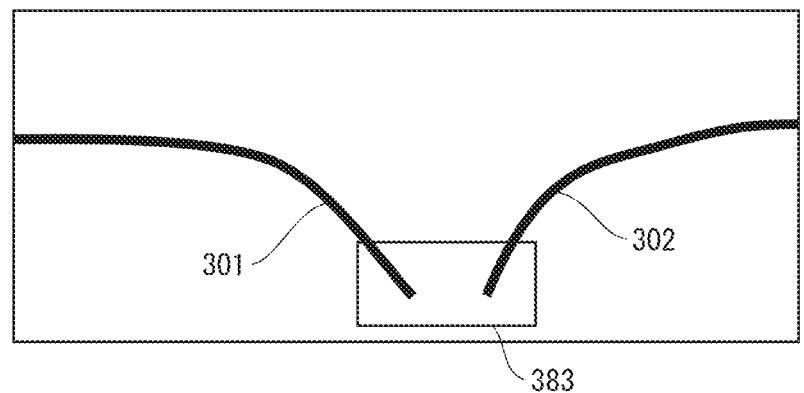
FIG. 12B illustrates an example of specification of a joint pertaining to the embodiment.

A joint is detected by the following method. FIG. 11 illustrates a bone surface 301 and a bone surface 302 that are detected. The joint is determined to be an interrupted portion in which the bone surface 301 and the bone surface 302 are not continuous (step S508 in FIG. 9). Note that two joint positions such as a joint position 381 and a joint position 382, as illustrated in FIG. 12A, may be specified, or a joint position 383 that encompasses two bone surfaces, as illustrated in FIG. 12B, may be specified.

A bone end is detected by the following method. First, a detection result of the bone surface 301 is smoothed. Curvature of each point on a bone surface is calculated. Finally, a point where the curvature of the bone surface 301 is positive and has a convex shape is detected as a bone end. Every bone has a bone end, and therefore the same process is performed with respect to the bone surface 302, and a bone end is detected. In FIG. 11, the locations surrounded by circles are such bone ends.

Figure 13:
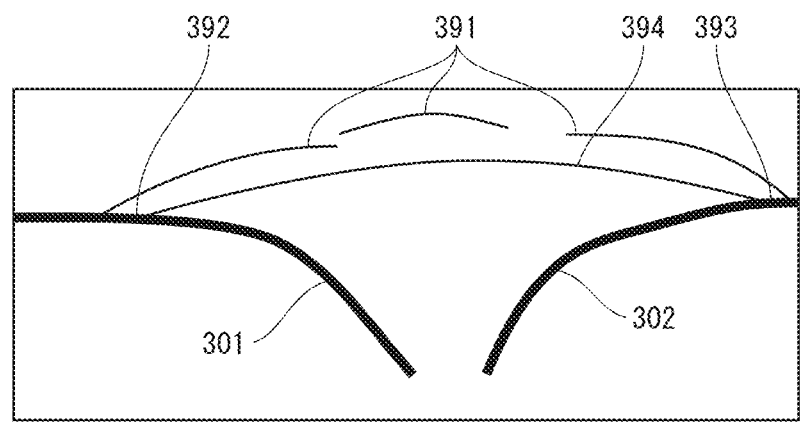
FIG. 13 illustrates an example of specification of an articular capsule pertaining to the embodiment.

An articular capsule is detected by the following method. FIG. 13 illustrates edges that are located less deeply on the ultrasound image than the bone surface 301, the bone surface 302, and the joint. Edges 391 and an edge 394 are edges that are located less deeply than an articular cavity region, the bone surface 301, and the bone surface 302. Anatomically, since the articular capsule 140 is connected to the bone 111 and the bone 121, as illustrated in FIG. 2, the articular capsule in the ultrasound image is also connected to the bone surface 301 and the bone surface 302. Further, an articular cavity region has a low luminance, while an articular capsule and a bone surface have high luminance. Thus, among edges detected in step S202, an edge that is connected to the bone surface 301 and the bone surface 302, and that along with the bone surface 301 and the bone surface 302 surrounds a region having a low luminance, is specified as an articular capsule. In FIG. 13, an articular capsule 394 is detected that contacts the bone surface 301 at a point 392 and contacts the bone surface 302 at a point 393. Specifically, as in the steps after step S509 in the flowchart in FIG. 9, with respect to an edge that is classified as belonging to a sinew segment, whether or not each end of the edge contacts a bone surface (the bone surface 301 and the bone surface 302) is determined (step S510). Further, whether or not a region surrounded by the edge, the bone surface 301, and the bone surface 302 has a low luminance is determined (step S511). If both determinations are positive, the edge is determined to be an articular capsule (step S512), and if at least one determination is negative, the edge is determined to be muscle fiber (step S513).

When an articular capsule is specified, a region that is surrounded by a bone surface (the bone surface 301 and the bone surface 302) and an articular capsule, and that has a low luminance, is determined to be an articular cavity region.

<Quantification of Disease Activity>

Figure 14:
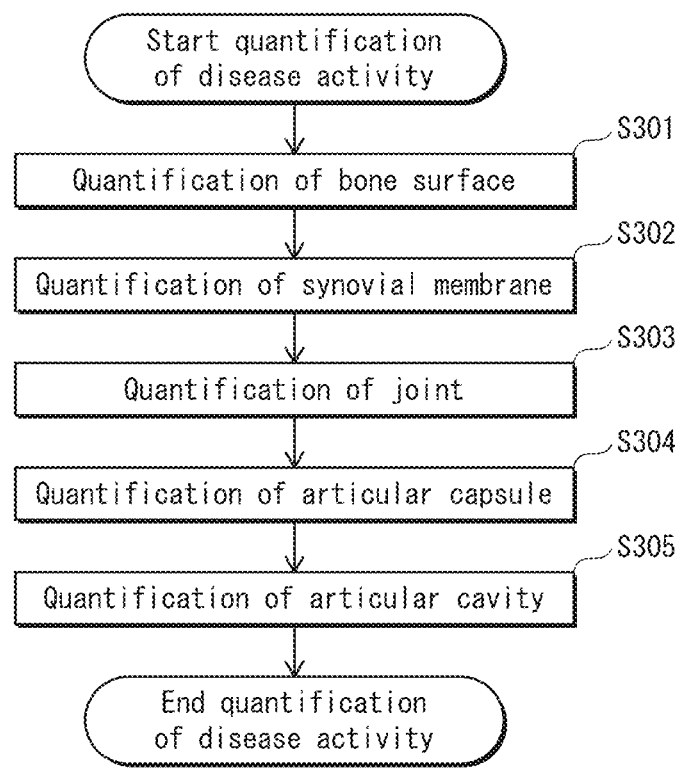
FIG. 14 is a flowchart illustrating a disease activity quantification operation of the ultrasound diagnostic device pertaining to the embodiment.

Quantification of disease activity in step S300 is described in detail below. FIG. 14 is a flowchart illustrating quantification of disease activity.

<<Quantification of Bone Surface>>

Figure 15:
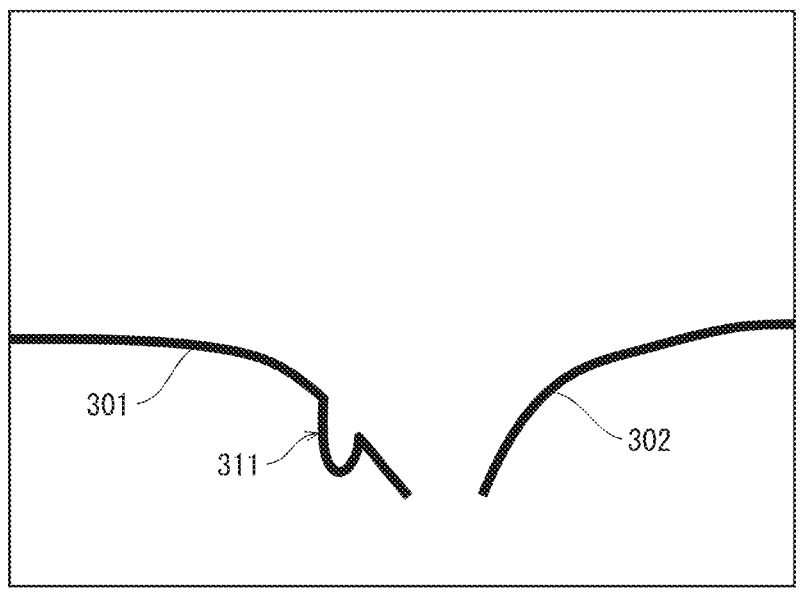
FIG. 15 illustrates bone erosion in an ultrasound image of a joint.

First, the pathology analyzer 26 performs quantification of a bone surface (step S301). As rheumatoid arthritis progresses, a bone erosion 311 becomes observable in the bone surface 301 as illustrated in FIG. 15. Accordingly, bone erosion can be extracted from the bone surface 301, and progress of the bone erosion can be quantitatively evaluated.

Figure 16A:
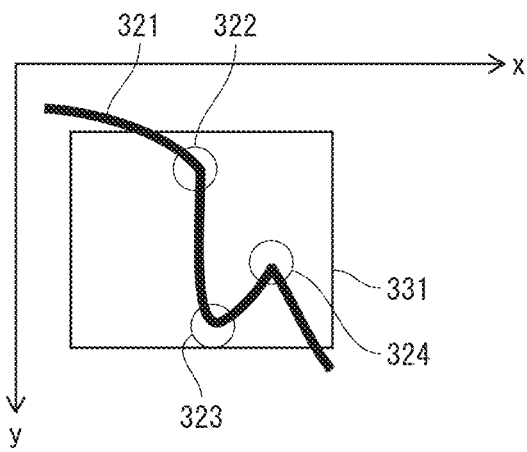
FIG. 16A illustrates detection of bone erosion pertaining to the embodiment.
Figure 16B:
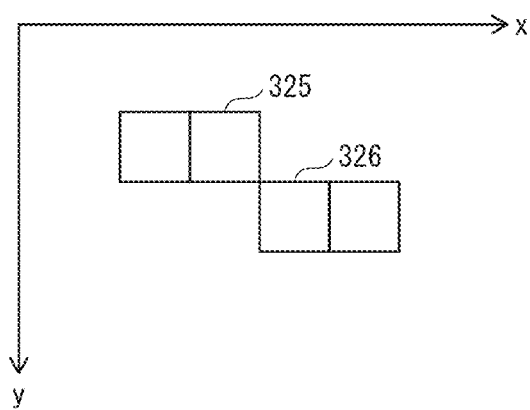
FIG. 16B is a conceptual diagram of a single-order differential used for detection of bone erosion.

First, the bone erosion 311 is extracted. The bone erosion 311 may be extracted as a point of the bone surface having local extrema values. As illustrated in FIG. 16A, a bone surface 321 in which bone erosion is present has a concave shape. This concavity is detected as extrema values of the bone surface. Specifically, as illustrated in FIG. 16B, a first order differential of the bone surface in the x axis direction and the y axis direction in the ultrasound image is calculated. In other words, a difference in x axis coordinates and a difference in y axis coordinates are calculated for a pixel i (illustrated as a pixel 325 in FIG. 16B) and a pixel (i+1) (illustrated as a pixel 326 in FIG. 16B) that is adjacent to the pixel i, and extrema values thereof are detected. More specifically, calculation is performed according to following formulae (Math 3).

$$\dot{x} = x_{i+1} - x_i$$

$$\dot{y} = y_{i+1} - y_i \qquad \text{[Math 3]}$$

First, from the origin of the x axis, first-order differentials of the bone surface 321 are calculated. A local extremum 322 is where a value of a first-order differential of the x axis direction greatly decreases, and a local extremum 323 is where the value returns to the original level. Further, from the local extremum 323 a sign of a first-order differential of the y axis inverts from minus to plus, and around a local extremum 324 inverts again, from plus to minus. Where a value of a first-order differential fluctuates greatly, or where a sign inverts between plus and minus multiple times within a local region such as a local region 331, the pathology analyzer 26 determines that bone erosion is present in such a region.

Figure 16C:
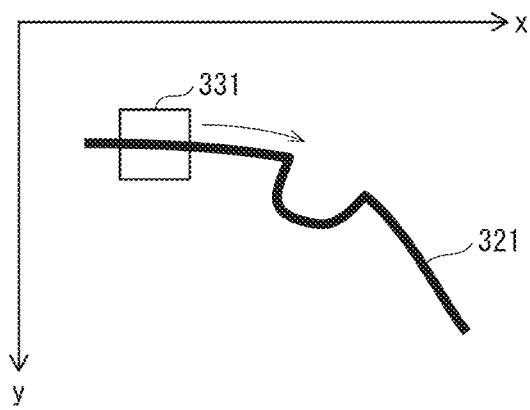
FIG. 16C illustrates a bone erosion detection operation.

A method of specifying a local region in which bone erosion is present is described below using FIG. 16C. First, the pathology analyzer 26 calculates a first-order differential of pixels of the bone surface 321 included in the local region 331, then determines whether or not bone erosion is included. Note that a first-order differential of a pixel is calculated in both an x axis direction and a y axis direction. Next, the local region 331 is moved a certain distance along the bone surface 321. By repeating these two operations, a local region in which bone erosion is present is automatically specified. On the other hand, when first-order differentials are calculated in the same way for a bone surface in which bone erosion is not present, the first-order differentials do not change greatly for the x axis or the y axis. Accordingly, extrema values do not occur, and the pathology analyzer 26 automatically determines that bone erosion is not present in the bone surface.

Figure 17A:
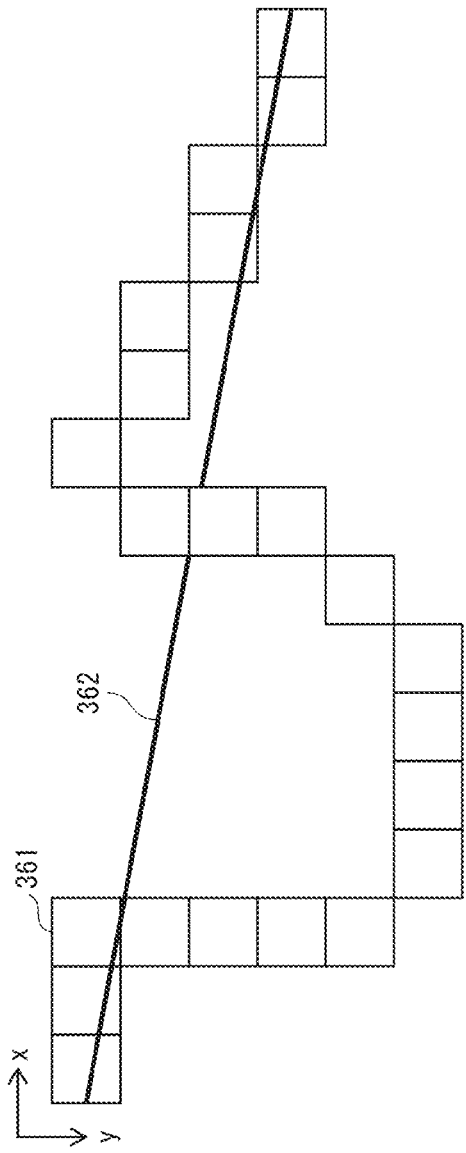
FIG. 17A illustrates quantification of a bone surface pertaining to the embodiment.
Figure 17B:
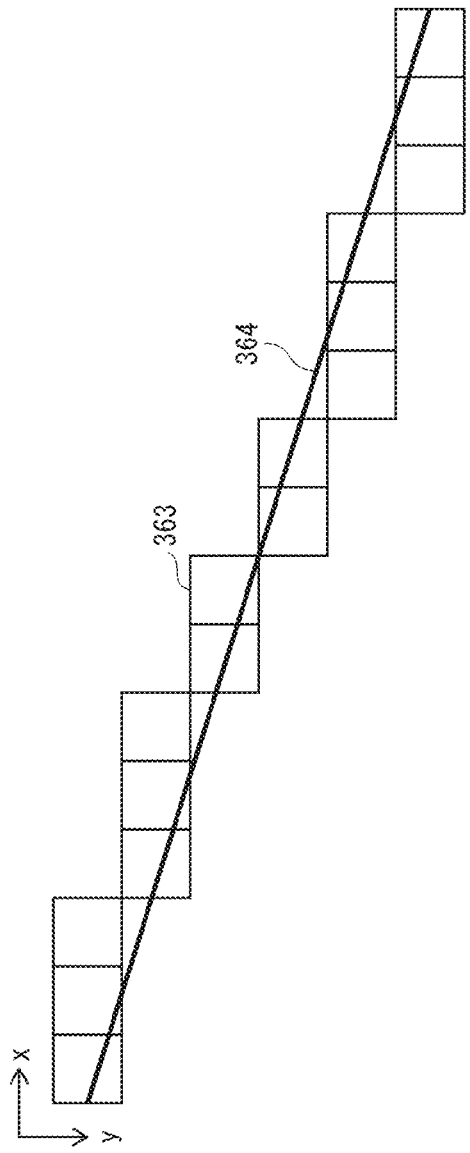
FIG. 17B illustrates quantification of a bone surface pertaining to the embodiment.

Next, quantification of detected bone erosion is performed. As one method of quantification of bone erosion, a function is fitted and a difference between the function and the bone surface is calculated. FIG. 17A illustrates a case where bone erosion exists, and illustrates a bone surface 361 and a fitting function 362. On the other hand, FIG. 17B illustrates a case where bone erosion does not exist, and illustrates a bone surface 363 and a fitting function 364. As illustrated in FIG. 17A and FIG. 17B, a case in which bone erosion is present has a larger fitting error, which is a difference between a bone surface and a fitting function, compared to a case in which bone erosion is not present. Further, as bone erosion progresses, smoothness of a bone surface is lost, and therefore the fitting error increases. Accordingly, the fitting error is an indicator of a degree of progression of bone erosion.

Here, any function may be used for fitting. However, a fitting function that fits a portion of bone erosion is not desirable and therefore care is required for selection of the fitting function. Note that when more than one bone erosion is present, a fitting error for each bone erosion may be applied individually, or a statistical quantity such as a maximum value, minimum value, total value, average value, median value, etc., of fitting errors of the bone erosions may be calculated.

Figure 18A:
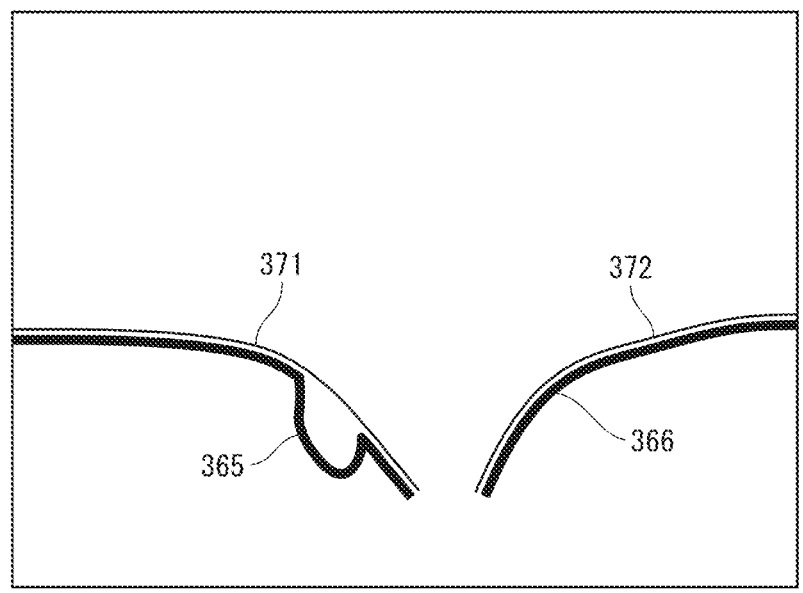
FIG. 18A illustrates quantification of a bone surface pertaining to the embodiment.

Further, as illustrated in FIG. 18A, a function may be fitted to an entire bone surface. Specifically, a deepest portion of the bone surface, or an interrupted portion (joint position) is separated into left and right, and a function is fitted to each of the left and the right portions. When a function is fitted to an entire bone surface, detection of a position of bone erosion is not required. FIG. 18A illustrates a function 371 that is fitted to a bone surface 365 and a function 372 that is fitted to a bone surface 366. When bone erosion is present, a fitting error between the function 371 and the bone surface 365 is large. In such a case, presence of bone erosion is known and evaluation of disease activity of rheumatoid arthritis is also performed by performing quantification by using the fitting error. Note that any function may be used for fitting. However, a fitting function that fits a portion of bone erosion is not desirable and therefore care is required for selection of the fitting function.

Figure 18B:
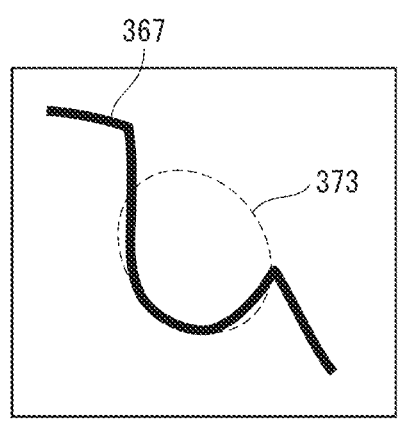
FIG. 18B illustrates quantification of bone erosion pertaining to the embodiment.

Alternatively, bone erosion may be directly quantified. FIG. 18B illustrates an elliptic function 373 fitted to a bone surface 367 in which a bone erosion is determined to be present. In such a case, for example, a least-squares method is used to determine a fitting function. In such a case, various geometric quantities of an ellipse, such as area, major axis, minor axis, eccentricity, etc., may be used as an index in quantification. Note that when more than one bone erosion is present, a quantification indicator for each bone erosion may be used, or a statistical quantity such as a maximum value, minimum value, total value, average value, median value, etc., of indicators after quantifying the bone erosions may be used.

<<Quantification of Synovial Membrane>>

Next, quantification of a synovial membrane is performed (step S302). FIG. 10B is a diagram illustrating quantification of a synovial membrane. Here, a synovial membrane that is detected is indicated as a region 481. Here, with respect to a bone end 308 and a bone end 309 detected in step S204, a straight line 482 connects the bone end 308 and the bone end 309, a straight line 483 through the bone end 308 is parallel to the y axis, and a straight line 484 through the bone end 309 is also parallel to the y axis.

As described above, when rheumatoid arthritis progresses, synovial membranes thicken. As a synovial membrane thickens, the synovial membrane thickens first towards skin, or in other words upwards in an ultrasound image. As thickening progresses further, the synovial membrane also broadens left and right in the ultrasound image. Here, a synovial membrane region not exceeding the straight line 482, the straight line 483, or the straight line 484, is given a score GS1. Further, a synovial membrane region exceeding the straight line 482, or extending as far as a region 485 above the joint surrounded by the straight line 482, the straight line 483, and the straight line 484, is given a score GS2. Furthermore, a synovial membrane region exceeding the straight line 483 or the straight line 484, or extending as far as at least one of a region 486 to the left of the straight line 483 and a region 487 to the right of the straight line 484, is given a score GS3. Note that although the region 481 illustrated in FIG. 10B, which indicates the synovial membrane, exceeds the straight line 482 and extends as far as the region 485, neither the straight line 483 nor the straight line 484 is exceeded, and therefore the pathology analyzer 26 determines that the synovial membrane has a score GS2.

<<Quantification of Joint>>

Next, a joint is quantified (step S303). As rheumatoid arthritis progresses, cartilage decreases, and therefore, as shown in FIG. 2, the bone 111 and the bone 121 become close to each other. Accordingly, in an ultrasound image, an interval between joint positions narrows. Thus, by quantifying the interval of the joint positions, disease activity of rheumatoid arthritis can be evaluated. Specifically, a distance or a horizontal distance (x coordinate difference) between the joint position 381 and the joint position 382, as shown in FIG. 12A, is quantified.

<<Quantification of Articular Capsule>>

Next, an articular capsule is quantified (step S304). As shown in FIG. 2, as rheumatoid arthritis progresses, the synovial membrane 130 thickens, and therefore the articular capsule 140 that encapsulates the synovial membrane 130 also enlarges. Accordingly, in an ultrasound image, the shape of an edge of the articular capsule changes. Accordingly, by quantifying a length, height, width, area, etc., of the articular capsule, disease activity of rheumatoid arthritis can be evaluated.

Figure 19A:
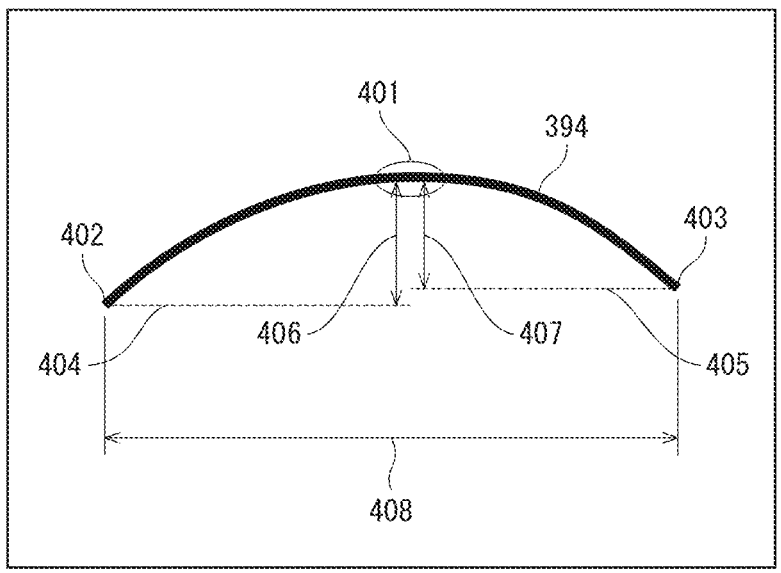
FIG. 19A illustrates an example of quantification of an articular capsule pertaining to the embodiment.
Figure 19B:
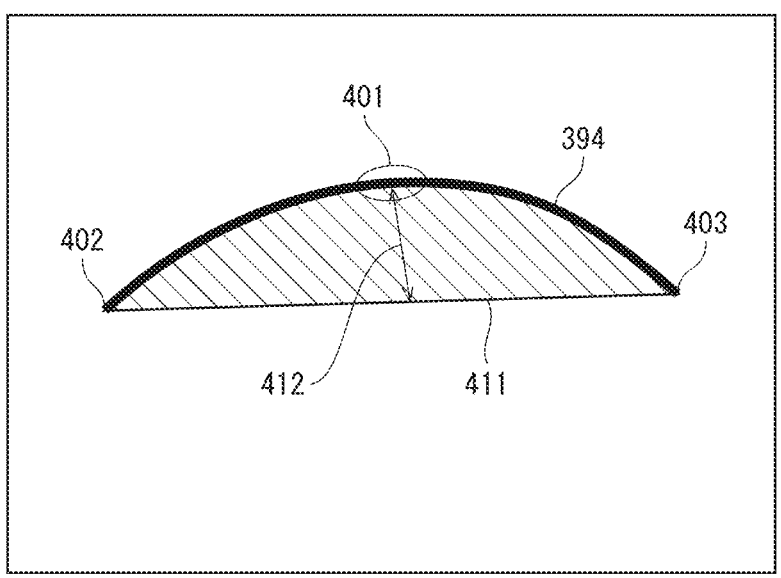
FIG. 19B illustrates an example of quantification of an articular capsule pertaining to the embodiment.

Methods of quantifying the length, the height, the width, and the area of the articular capsule are described using FIG. 19A and FIG. 19B.

The length of the articular capsule is quantified using a length of an edge 394 of the articular capsule.

The height of the articular capsule is quantified as a length of a perpendicular line 406 that is perpendicular to a horizontal line 404 that passes through a left end 402 of the edge 394, and as a length of a perpendicular line 407 that is perpendicular to a horizontal line 405 that passes through a right end 403 of the edge 394. The length of the perpendicular line 406 is measured from an extremum value 401 that is at the smallest value of a y coordinate of the edge 394 to the horizontal line 404, and the length of the perpendicular line 407 is measured from the extremum value 401 to the horizontal line 405. Note that both lengths may be used individually, or a statistical quantity such as a maximum value, a minimum value, an average value, a total value, etc., may be used. Alternatively, as illustrated in FIG. 19B, the height of the articular capsule may be quantified as a length of a perpendicular line 412 that is perpendicular to a straight line 411 that connects the left end 402 of the edge 394 to the right end 403 of the edge 394. The length of the perpendicular line 412 is measured from the extremum value 401 to the straight line 411.

The width of the articular capsule is quantified using a horizontal distance 408 (x coordinate difference) between the left end 402 and the right end 403, or alternatively, a length of the straight line 411 that connects the left end 402 and the right end 403.

The area of the articular capsule is quantified using an area of a region surrounded by the edge 394 and the straight line 411, or in other words a number of pixels within the region surrounded by the edge 394 and the straight line 411.

Note that locations of the left end 402 and the right end 403 of the edge 394 of the articular capsule are coordinates detected in step S509, and the extremum value 401 is, among pixels included in the edge 394, a pixel whose y coordinate value is lowest. However, the left end 402, the right end 403, and the extremum value 401 may be set through the input 31 by a user.

<<Quantification of Articular Cavity Region>>

Figure 21A:
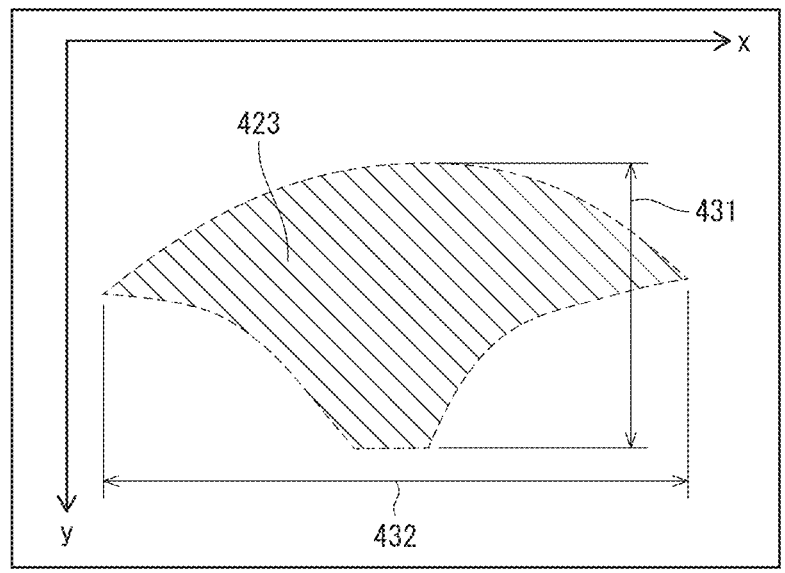
FIG. 21A illustrates an example of quantification of an articular cavity region pertaining to the embodiment.
Figure 21B:
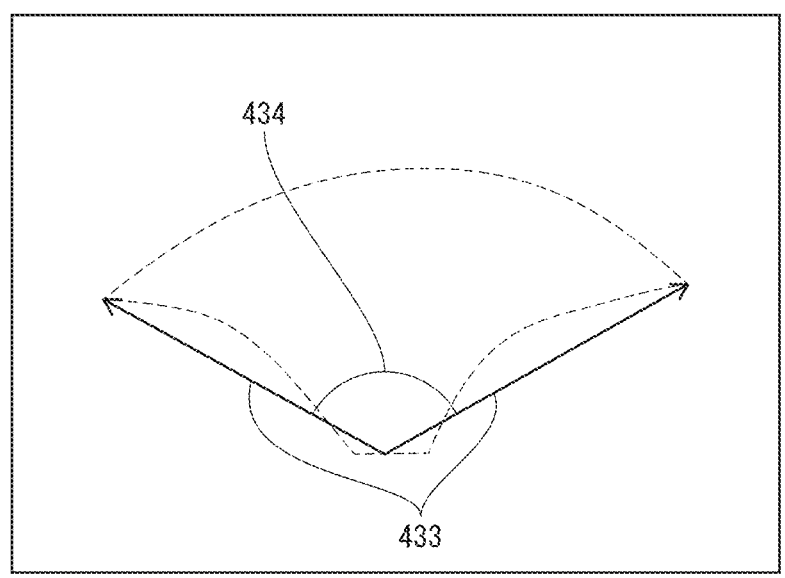
FIG. 21B illustrates an example of quantification of an articular cavity region pertaining to the embodiment.

Next, an articular cavity region is quantified (step S305). An indicator for quantifying the articular cavity region may be an area, height, width, or angle of the articular cavity region. In FIG. 21A, an articular cavity region 423, an articular cavity region height 431, and an articular cavity region width 432 are illustrated. In FIG. 21B, arrows 433 that extend from a joint position to two ends of the articular capsule and an angle 434 of the articular cavity region are illustrated.

The area of the articular cavity region is quantified by a count of pixels within the articular cavity region 423.

The width of the articular cavity region is quantified by a difference between a maximum value and a minimum value of x coordinates in pixels within the articular cavity region 423, or alternatively a difference (horizontal distance) between x coordinates of a left end and a right end of the articular capsule.

The height of the articular cavity region is quantified by a difference between a maximum value and a minimum value of y coordinates in pixels within the articular cavity region 423.

The angle of the articular cavity region is quantified by the angle 434 between the two arrows 433 that each extend to one of two ends of the articular cavity region from a center of a joint position. Specifically, the center point between the joint position 381 and the joint position 382, specified in step S204, is used as the center of the joint position. Note that for the two ends of the articular cavity region, ends of the articular capsule 394 specified in step S204 may be used, or coordinates used to quantify the width of the articular cavity region may be used. Specifically, coordinates with the highest x coordinate value and coordinates with the lowest x coordinate value may be used.

Figure 22:
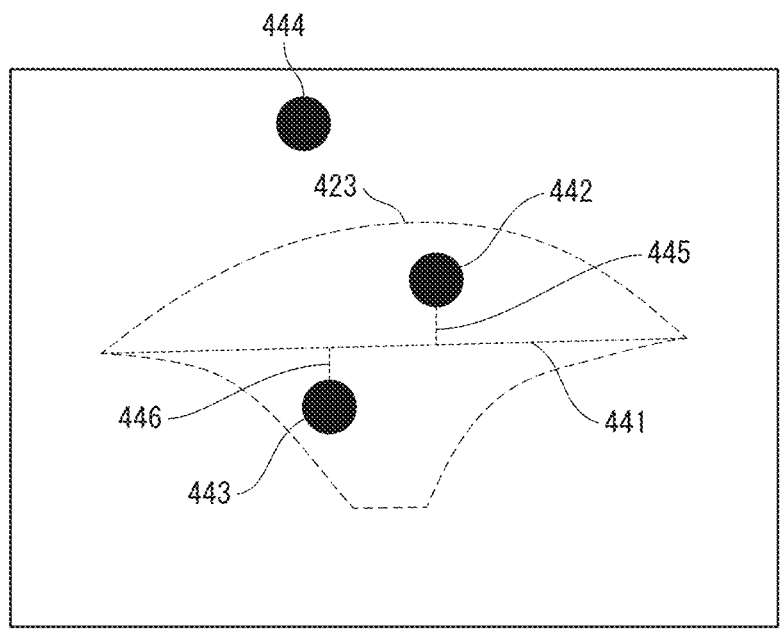
FIG. 22 illustrates an example of quantification of an articular cavity region pertaining to the embodiment.

Further, quantification of the articular cavity region may be performed using a power Doppler image including blood-flow signals. As rheumatoid arthritis progresses, angiogenesis occurs in the synovial membrane, and therefore a blood-flow signal may be detected in the synovial membrane region. FIG. 22 illustrates a blood-flow signal 442, a blood-flow signal 443, and a blood-flow signal 444 in a power Doppler image. As an indicator in quantification, the following may be used: a total area of the blood-flow signal 442 and the blood-flow signal 443 observed inside the articular cavity region 423; a proportion of the total area of the blood-flow signal 442 and the blood-flow signal 443 with respect to the area of the articular cavity region 423; a number of blood-flow signals measured as a continuous region; or other indicators. Note that since the blood-flow signal 444 is outside the region of the articular cavity region 423, the blood-flow signal 444 is not subject to quantification.

Further, position of blood-flow signals may be subject to quantification. This is because, as rheumatoid arthritis progresses, the synovial membrane thickens, and therefore a blood-flow signal may be observed in an upper portion of the articular cavity region. First, a straight line that crosses the articular cavity region 423 is set as a boundary line 441 that divides the articular cavity region 423 into an upper portion and a lower portion. Note that for the two ends of the boundary line 441, as in the quantification of the width and angle of the articular cavity region described above, ends of the articular capsule 394 specified in step S204 may be used, or coordinates used to quantify the width of the articular cavity region, i.e., coordinates of the pixel with the highest x coordinate value and coordinates of the pixel with the lowest x coordinate value may be used. Further, the boundary line 441 may be inputted via the input 31 by a user. Next, the blood-flow signal 442 that is above the boundary line 441 and the blood-flow signal 443 that is below the boundary line 441 are separated into two categories. In each region, the following are quantified: a total area of a blood-flow signal, a proportion of a total area of the blood-flow signal with respect to an area of the articular cavity region 423, and a number of blood-flow signals measured as a continuous region.

Further, different coefficients may be set for a blood-flow signal positioned above the boundary line 441 and a blood-flow signal positioned below the boundary line 441, and quantification may be performed by calculating a weighted average according to the following formula (Math 4).

$$\text{Value} = \omega_1 Q_1 + \omega_2 Q_2 \qquad [\text{Math 4}]$$

Here, $\omega_1$ is a coefficient allocated to a blood-flow signal positioned above the boundary line 441, $Q_1$ is a quantification value derived from the blood-flow signal positioned above the boundary line 441, $\omega_2$ is a coefficient allocated to a blood-flow signal positioned below the boundary line 441, and $Q_2$ is a quantification value derived from the blood-flow signal positioned above the boundary line 441. $Q_1$ is a total area of the blood-flow signal in the upper portion, a proportion of the total area of the blood-flow signal with respect to an area of the articular cavity region 423, or a number of blood-flow signals measured as a continuous region. $Q_2$ is similar, with respect to the lower portion. Q1 and Q2 preferably use a same type of quantification evaluation value.

Further, a vertical distance from the boundary line 441 to a position of a blood-flow signal may be used for quantification. As illustrated in FIG. 22, a length of a vertical line 445 from the blood-flow signal 442 to the boundary line 441 and a length of a vertical line 446 from the blood-flow signal 443 to the boundary line 441 may be evaluation values. In such a case, quantification is performed such that, with respect to a blood-flow signal above the boundary line 441, a higher evaluation value is provided as distance from the boundary line 441 increases, with respect to a blood-flow signal below the boundary line 441, a lower evaluation value is provided as distance from the boundary line 441 increases, and by using a total of the evaluation values. Further, weighting may be performed using the evaluation values that depend on distance. For example, for each blood-flow signal, weighting may be performed on the area of the blood-flow signal according to the following formula (Math 5), where $l_n$ is an evaluation value based on distance from the boundary line 441 to the blood-flow signal, and $V_n$ is an area of the blood-flow signal.

$$\text{Value} = \Sigma l_n V_n \qquad [\text{Math 5}]$$

In such a case, a quantification value is defined that comprehensively evaluates position and area of blood flow. Note that $V_n$ may also be a proportion of a total area of the blood-flow signal with respect to an area of the articular cavity region 423, or a number of blood-flow signals observed as a continuous region. Further, for each blood-flow signal, $l_n$ may be a straight-line distance from a center of a joint position to the blood-flow signal. In such a way, an evaluation value that is higher as distance from the center of the joint position increases and an evaluation value that is lower as distance from the joint position decreases are used.

<Summary>

According to the above configuration, each feature line that indicates a boundary between components is detected in an independent form, and a set of multiple feature lines are allocated to boundaries of components. Thus, boundary lines of components, in other words a bone surface, skin, and articular cavity, correspond to one or more of the feature lines. Thus, when compared to a case in which one edge is detected as a line image, pattern matching is not required, and therefore situations are avoided where an appropriate comparison pattern does not exist and a determination cannot be made, and an inappropriate comparison pattern is used and incorrect recognition of a boundary is performed. Further, when compared to a case in which an edge is detected using only luminance, a situation is avoided where an edge is incorrectly recognized due to a high luminance edge being in close proximity to another edge or high luminance noise overlapping an edge.

Furthermore, an amount of calculation is successfully reduced due to a lot of calculation, such as pattern matching calculation, not being required.

Thus, each component is detected with high accuracy, and quantification of pathology having high reliability is performed independently of an examiner.

Modifications Pertaining to the Embodiment (1) In the embodiment, the ultrasound diagnostic device 20 performs quantification of disease activity with respect to all of the bone surface, synovial membrane, joint, articular capsule, and articular cavity region. However, the present invention is not limited in this way. The ultrasound diagnostic device 20 may, for example, from among the bone surface, synovial membrane, joint, articular cavity, and articular cavity region, quantify only some of the above, or may quantify only disease activity as specified by a user using the input 31. Note that components that are not required to be specified when performing quantification are not required to be detected. For example, when the synovial membrane is not quantified, the synovial membrane may also not be detected.

Further, the ultrasound diagnostic device 20 may perform only detection of components without performing quantification, and quantification processing, etc., may be performed by an external device.

(2) In the embodiment, the ultrasound diagnostic device 20 uses the ultrasound probe 11 to acquire an ultrasound image, and performs detection of components and quantification of disease activity with respect to the image so acquired. However, the present invention is not limited in this way. The ultrasound diagnostic device 20 may, for example, store a plurality of ultrasound images in the storage 23, acquire an ultrasound image from the storage 23, and perform detection of components and quantification of disease activity with respect to the ultrasound image so acquired. Alternatively, for example, the ultrasound diagnostic device 20 may acquire an ultrasound image from an external hard disk, SD card or other memory device, server on a network, network access storage (NAS) or other external storage, etc., and perform detection of components and quantification of disease activity with respect to the ultrasound image so acquired.

(3) In the embodiment, the ultrasound diagnostic device 20 detects the articular cavity region 423 by specifying the articular capsule 394. However, the present invention is not limited in this way. For example, in a case in which the articular capsule is not quantified, as described below, the articular cavity region may be detected directly without detecting the articular capsule, by using joint positions.

Figure 20A:
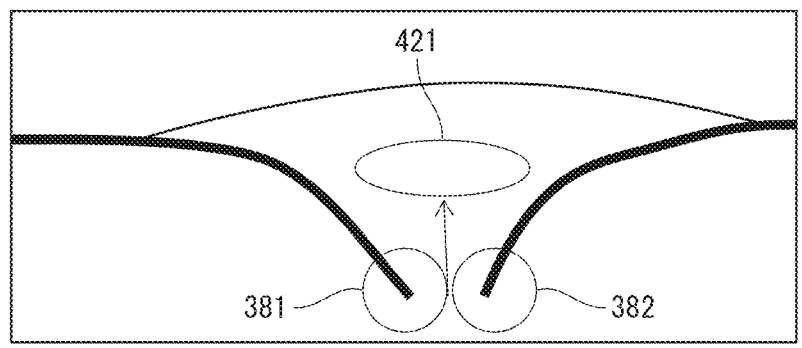
FIG. 20A illustrates an example of specification of an articular cavity region pertaining to a modification.
Figure 20B:
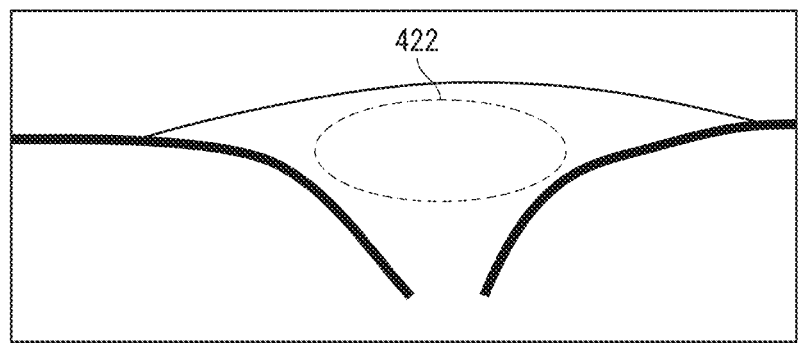
FIG. 20B illustrates an example of specification of an articular cavity region pertaining to the modification.
Figure 20C:
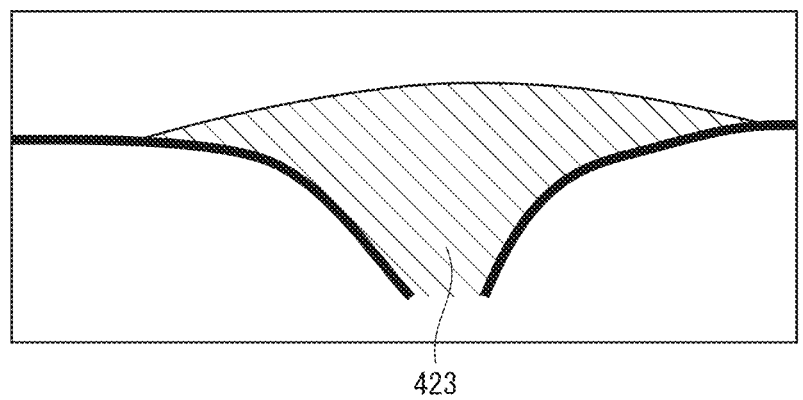
FIG. 20C illustrates an example of specification of an articular cavity region pertaining to the modification.

Specifically, using a low luminance of the articular cavity region in the ultrasound image compared to a bone surface or the articular capsule, the articular cavity region rendered in low luminance may be detected by a dynamic contour model, region expansion method, etc. As illustrated in FIG. 20A, using the joint position 381 and the joint position 382 specified in step S205, an initial search point 421 may be set above a center point between the joint position 381 and the joint position 382, for example, and a region rendered by low luminescence may be iteratively expanded from the initial search point 421. FIG. 20B illustrates an expanded search region 422. In this way, an articular cavity region 423 can be detected, as illustrated in FIG. 20C. Note that in the above detection, the bone surface 301 and the bone surface 302 specified in step S205 may be used.

Note that although the initial search point 421 is described as being above the point between the joint position 381 and the joint position 382, the initial search point 421 may be the point between the joint position 381 and the joint position 382, or may be set by a user using the input 31.

(4) In the embodiment, in steps S405-S415, processing order of the search start point is not mentioned. For example, processing may be performed in order from the bottom of the ultrasound image, or in order from the highest luminance. In this way, after accurately extracting a bone surface and skin, which are rendered by high luminescence, an articular capsule, etc., may be specified.

(5) In the embodiment, prior to detection of edges in step S202, enhancement processing of edges is performed in step S201. However, the present invention is not limited in this way. For example, enhancement processing of edges need not be performed.

Further, each time a single edge is detected in step S202, the following steps may be performed: (i) specify whether the edge is a boundary of a component, (ii) after eliminating the edge detected in step S202 from the ultrasound image, again perform the edge enhancement in step S201, and (iii) again perform the edge detection in step S202. Alternatively, after determining a boundary of a component to which each edge corresponds in step S205, edge enhancement in step S201 may be performed again after eliminating edges other than specified edges, and the specified edges may be re-detected in step S202. In this way, detection accuracy of edges is improved.

(6) In the embodiment, the edge detector 24 links a corresponding point corresponding to a minimum Value according to Math 2 to a search start point. However, the present invention is not limited in this way. As long as the Value is lower when luminance of the corresponding point is higher, and lower when distance between the search start point and the corresponding point is shorter or a difference between y coordinates of the search start point and the corresponding point is lower, the Value may, for example, be a value obtained by dividing the distance between the search start point and the corresponding point by the luminance of the corresponding point.

(7) In the embodiment, the edge detector 24 links a corresponding point having an x coordinate differing by one from that of a single-pixel search start point. However, the present invention is not limited in this way. For example, the search start point may be a pixel group of two-by-two pixels, and the corresponding point may be a pixel group of the same size whose upper-left pixel has an x coordinate differing by two from an upper-left pixel of the pixel group of the search start point. In such a case, luminance of a pixel group may be a luminance value of a pixel specified in the pixel group, such as an upper-left pixel, or may be a statistical value such as an average value, highest value, median value, etc., of the luminance of all pixels in the pixel group. Further, size of a pixel group is not limited to two-by-two pixels. In a range that does not affect accuracy of edge detection, the size of the pixel group may be four-by-four pixels, three-by-two pixels, or any other size.

(8) In the embodiment, quantification of the articular cavity region by using a power Doppler image that includes a blood-flow signal is described. Similarly, for example, quantification of the synovial membrane may be performed by using a power Doppler image that includes a blood-flow signal. In other words, quantification may be performed of: a total area of the blood-flow signal 442 and the blood-flow signal 443 observed inside the region 481 of the synovial membrane; a proportion of the total area of the blood-flow signal 442 and the blood-flow signal 443 with respect to an area of the region 481 of the synovial membrane; a number of blood-flow signals measured as a continuous region; etc. Further, quantification of the synovial membrane may be performed using Math 4 and Math 5. As rheumatoid arthritis progresses, angiogenesis occurs in the synovial membrane. Therefore, disease activity may be evaluated with greater accuracy by making such modifications.

(9) In the embodiment, the edge detector 24 searches for a corresponding point starting from a search start point having a lowest x coordinate and in a direction of increasing x coordinate value, but the present invention is not limited in this way. For example, the edge detector 24 may search for a corresponding point starting from a search start point have a highest x coordinate and in a direction of decreasing x coordinate value. Further, the edge detector 24 may search for a corresponding point starting from a search start point and in both a direction of increasing x coordinate value and a direction of decreasing x coordinate value, which enables detecting an edge that reverses direction along the x axis. In such a case, in detection of bone erosion, instead of detecting whether or not a first-order differential value of an x axis direction greatly fluctuates, the edge detector 24 may detect whether or not a sign of the first-order differential of the x axis direction changes (from plus to minus or vice-versa).

(10) The components of the ultrasound diagnostic devices pertaining to the embodiment and the modifications may, in whole or in part, be implemented as an integrated circuit of one chip or a plurality of chips, be implemented as a computer program, and be implemented in any other form. For example, the entire ultrasound diagnostic device may be implemented as one chip, or the image generator may be implemented as one chip and the component specifier, etc., implemented as another chip.

In a case in which implementation is achieved by an integrated circuit, implementation may typically be achieved as a large scale integration (LSI). Here, an LSI may variously be referred to as an IC, system LSI, super LSI, or ultra LSI, depending on the degree of integration.

Further, circuit integration methods are not limited to LSI, and implementation may be achieved by a dedicated circuit or general-purpose processor. Alternatively, a field programmable gate array (FPGA) that is programmable after LSI manufacture, and/or reconfigurable processor that allows reconfiguring of connections and settings of internal circuit cells may be used.

Furthermore, if circuit integration technology to replace LSI arises due to progress in semiconductor technology and other derivative technologies, such technology may of course be used to perform integration of function blocks.

Further, the ultrasound diagnostic devices pertaining to the embodiment and the modifications may be implemented by a program stored on a storage medium and a computer that reads and executes the program. The storage medium may be any kind of storage medium, such as a memory card, CD-ROM, etc. Further, the ultrasound diagnostic device pertaining to the present invention may be implemented by a program downloadable across a network and a computer that downloads the program across the network and executes the program.

(11) The embodiment described above illustrates one specific preferred example of the present invention. The values, forms, materials, components, component positions and connections, steps, step order, etc., illustrated in the embodiment represent examples and do not limit the spirit of the present invention. Further, among components in the embodiment, components not disclosed in the independent claims reciting top-level concepts of the present invention are described as components that may or may not be included, but when included contribute to a preferable form of implementation.

Further, to aid in understanding the invention, the scale of components in each drawing referred to in the embodiment may differ from actual implementation. Further, disclosure of the above embodiment is not a limitation and may be appropriately changed within the scope of the spirit of the present invention.

Furthermore, although members such as circuit parts, lead wires, etc., do exist on a substrate of an ultrasound diagnostic device, such electrical wiring and electric circuits may be implemented in various ways based on common knowledge in the technical field, and are therefore omitted from the description as they have no direct relevance to description of the present invention. Note that each drawing described above is schematic, and is not an exact representation.

<Supplement>

The following is a description of the configuration and effects of an ultrasound diagnostic device, an image processing method of an ultrasound diagnostic device, and a computer-readable non-transitory storage medium, each of which pertains to one aspect of the present invention.

(1) The ultrasound diagnostic device pertaining to one aspect of the present invention specifies, from an ultrasound image of a subject that includes a joint, a joint image portion that indicates components of the joint, the ultrasound diagnostic device including: an image processing circuit that acquires the ultrasound image and specifies the joint image portion, including: an ultrasound image acquirer that acquires the ultrasound image; and a component specifier that specifies an image portion indicating a boundary between the components, wherein when a first direction is a depth direction substantially perpendicular to a surface of the subject, a second direction is a direction orthogonal to the first direction, a first pixel is a pixel at a pixel location N in the second direction, a second pixel is a pixel at a pixel location N+1 in the second direction, and N is a positive integer, the component specifier detects one or more feature lines from the ultrasound image by repeatedly, while incrementing N, linking the first pixel with the second pixel when luminance of the second pixel is high and the second pixel is in close proximity to the first pixel, and specifies which of the one or more feature lines indicates a boundary between components, based on an order in the first direction of the one or more feature lines.

Further, the image processing method of an ultrasound diagnostic device pertaining to one aspect of the present invention is an image processing method of an ultrasound diagnostic device that specifies, from an ultrasound image of a subject that includes a joint, a joint image portion that indicates components of the joint, the image processing method including: acquiring the ultrasound image, specifying an image portion indicating a boundary between the components, wherein when a first direction is a depth direction substantially perpendicular to a surface of the subject, a second direction is a direction orthogonal to the first direction, a first pixel is a pixel at a pixel location N in the second direction, a second pixel is a pixel at a pixel location N+1 in the second direction, and N is a positive integer, the specifying includes: detecting one or more feature lines from the ultrasound image by repeatedly, while incrementing N, linking the first pixel with the second pixel when luminance of the second pixel is high and the second pixel is in close proximity to the first pixel, and specifying which of the one or more feature lines indicates a boundary between components, based on an order in the first direction of the one or more feature lines.

Further, the computer-readable non-transitory storage medium pertaining to one aspect of the present invention stores a program that causes a processor to execute image processing, the processor being used by an ultrasound diagnostic device that specifies, from an ultrasound image of a subject that includes a joint, a joint image portion that indicates components of the joint, the image processing including: acquiring the ultrasound image; and specifying an image portion indicating a boundary between the components, wherein when a first direction is a depth direction substantially perpendicular to a surface of the subject, a second direction is a direction orthogonal to the first direction, a first pixel is a pixel at a pixel location N in the second direction, a second pixel is a pixel at a pixel location N+1 in the second direction, and N is a positive integer, the specifying includes: detecting one or more feature lines from the ultrasound image by repeatedly, while incrementing N, linking the first pixel with the second pixel when luminance of the second pixel is high and the second pixel is in close proximity to the first pixel, and specifying which of the one or more feature lines indicates a boundary between components, based on an order in the first direction of the one or more feature lines.

In this way, each feature line indicating a boundary of a component is detected in an independent form, and therefore pattern matching to associate sets of multiple feature lines with boundaries of components is not required. Thus, a boundary line of a component corresponds to a feature line, and regardless of a form of the feature line, a boundary between one component and another component is accurately detected. Further, even if a form of an image portion indicating a joint differs greatly from a typical form of an image indicating a joint, an order of each component in the depth direction does not change. Therefore, each component is accurately specified without mistaking one component for another.

(2) Further, the ultrasound diagnostic device (1) pertaining to one aspect of the present invention may be configured such that the component specifier specifies, from one of the one or more feature lines that is deep in the first direction, a bone surface as a boundary between the components, and further specifies, from a region in which the one or more feature lines are not detected that is less deep in the first direction than the bone surface, and based on a change of luminance in the first direction, an image portion indicating a synovial membrane.

In this way, from the bone surface and the ultrasound image, a synovial membrane region is detected.

(3) Further, the ultrasound diagnostic device (1) pertaining to one aspect of the present invention may be configured such that the first direction is parallel with a y axis and the second direction is parallel with an x axis, the first pixel is a pixel having a local maximum luminance relative to other pixels in the first direction, or a pixel linked with the first pixel in a previous iteration of the linking, and the second pixel is a pixel among pixels having an x coordinate of N+1 that has a lowest Value according to Value=$m \cdot L(N+1, y) + n \cdot |y - y_N|$ where $(N, y_N)$ are coordinates of the first pixel, $L(N+1, y)$ is luminance of a given pixel having an x coordinate of N+1, (N+1, y) are coordinates of the given pixel, and m and n satisfy n>0>m.

In this way, a feature line is detected by repeatedly, while incrementing x, linking a pixel having a high luminance and a small difference in coordinates in the y axis direction.

(4) Further, the ultrasound diagnostic device (3) pertaining to one aspect of the present invention may be configured such that the image processing circuit further includes an edge enhancer, and the component specifier detects the one or more feature lines by the linking of the first pixel with the second pixel being performed based on a result of the edge enhancer performing edge enhancement on the ultrasound image.

In this way, a boundary between components is enhanced by the edge enhancer, and therefore the boundary between components is detected with greater accuracy.

(5) Further, the ultrasound diagnostic device (1) pertaining to one aspect of the present invention may be configured such that the component specifier detects a plurality of feature lines from the ultrasound image by repeatedly performing detection of one feature line from the ultrasound image, and detection of a new feature line is performed after eliminating a previously detected feature line from the ultrasound image.

In this way, pixels pertaining to a feature line that is already detected do not affect detection of another feature line, and therefore a boundary between components is detected with greater accuracy.

(6) Further, the ultrasound diagnostic device (1) pertaining to one aspect of the present invention may be configured such that the component specifier, when specifying the image portion indicating the boundary between the components: classifies a feature line that is shallow in the first direction as belonging to a skin segment, and classifies a feature line that is deep in the first direction as belonging to a bone segment; and specifies an image portion indicating skin from the feature line classified as belonging to the skin segment, and an image portion indicating a bone surface from the feature line classified as belonging to the bone segment.

In this way, based on anatomical order, a feature line is classified as belonging to a segment, and thus a specification is made of a boundary between components that a detected feature line corresponds to.

(7) Further, the ultrasound diagnostic device (6) pertaining to one aspect of the present invention may be configured such that the component specifier further specifies, as an image portion indicating an articular capsule, a feature line that is shallower in the first direction than the bone surface, both ends of the feature line being in close proximity to the bone surface.

In this way, the image portion indicating the articular capsule is specified based on a detected bone surface and anatomy.

(8) Further, the ultrasound diagnostic device (6) pertaining to one aspect of the present invention may be configured such that the component specifier further specifies, when the bone surface has an interrupted portion and the interrupted portion of the bone surface is deeper in the first direction than other portions of the bone surface, a center of the interrupted portion as indicating a center of a joint position in the second direction.

In this way, the image portion indicating the joint position is specified based on a detected bone surface and anatomy.

(9) Further, the ultrasound diagnostic device (7) pertaining to one aspect of the present invention may be configured such that the component specifier further specifies a region between the articular capsule and the bone surface as an image portion indicating an articular cavity region.

In this way, the image portion indicating the articular cavity region is specified based on a detected joint position and anatomy.

(10) Further, the ultrasound diagnostic device (6) pertaining to one aspect of the present invention may further include a pathology analyzer that performs quantification of disease activity in the bone surface by using the image portion indicating the bone surface specified by the component specifier.

In this way, quantification of disease activity is performed based on a shape of the bone surface.

(11) Further, the ultrasound diagnostic device (10) pertaining to one aspect of the present invention may be configured such that the pathology analyzer quantifies a smoothness of the bone surface.

In this way, quantification of disease activity is performed based on the smoothness of the bone surface.

(12) Further, the ultrasound diagnostic device (11) pertaining to one aspect of the present invention may be configured such that the pathology analyzer fits a predefined function to the image portion indicating the bone surface, and quantifies a difference between the image portion indicating the bone surface and the predefined function as the smoothness of the bone surface.

In this way, the shape and the smoothness of the bone surface is quantified.

(13) Further, the ultrasound diagnostic device (10) pertaining to one aspect of the present invention may be configured such that the pathology analyzer quantifies bone erosion of the bone surface.

In this way, quantification of disease activity is performed based on the bone erosion of the bone surface.

(14) Further, the ultrasound diagnostic device (13) pertaining to one aspect of the present invention may be configured such that the pathology analyzer calculates a first-order differential of the first direction or the second direction in the image portion indicating the bone surface, specifies an image portion indicating the bone erosion based on variation of the first-order differential, fits a predefined function to the image portion indicating the bone erosion, and quantifies a difference between the image portion indicating the bone erosion and the predefined function as a smoothness of the bone surface.

In this way, a position of the bone erosion is specified, and the shape and the smoothness of the bone surface is quantified based on the shape of the bone erosion.

(15) Further, the ultrasound diagnostic device (8) pertaining to one aspect of the present invention may further include a pathology analyzer that performs quantification of disease activity in the joint by using the image portion indicating the bone surface specified by the component specifier, wherein the pathology analyzer quantifies a straight-line length or a horizontal length of the interrupted portion of the bone surface.

In this way, quantification of disease activity is performed based on a shape of the joint.

(16) Further, the ultrasound diagnostic device (7) pertaining to one aspect of the present invention may further include a pathology analyzer that performs quantification of disease activity in the articular capsule by using the image portion indicating the articular capsule specified by the component specifier, wherein the pathology analyzer quantifies at least one of a thickness, width, length, and area of the articular capsule.

In this way, quantification of disease activity is performed based on a shape of the articular capsule.

(17) Further, the ultrasound diagnostic device (16) pertaining to one aspect of the present invention may be configured such that the pathology analyzer quantifies, as the thickness of the articular capsule, (i) a difference between a coordinate having a highest value in the first direction of an image portion indicating the articular capsule and a coordinate in the first direction of an end point of the image portion indicating the articular capsule, or (ii) a distance from the coordinate having the highest value in the first direction of the image portion indicating the articular capsule to a straight line connecting both ends of the image portion indicating the articular capsule, as the width of the articular capsule, a coordinate difference along the second direction of coordinates at both ends of the image portion indicating the articular capsule, as the length of the articular capsule, a length from one end of a feature line indicating the articular capsule to another end of the feature line, and as the area of the articular capsule, an area surrounded by a straight line connecting both ends of the image portion indicating the articular capsule and the feature line indicating the articular capsule.

In this way, based on a feature point of an image indicating a detected articular capsule, disease activity of the articular capsule is quantified.

(18) Further, the ultrasound diagnostic device (9) pertaining to one aspect of the present invention may further include a pathology analyzer that performs quantification of disease activity in the articular cavity region by using the image portion indicating the articular cavity region specified by the component specifier, wherein the pathology analyzer quantifies at least one of a height, width, area, and shape of the articular cavity region.

In this way, quantification of disease activity is performed based on a shape of the articular cavity region.

(19) Further, the ultrasound diagnostic device (18) pertaining to one aspect of the present invention may be configured such that the pathology analyzer quantifies, as the height of the articular cavity region, a difference between a smallest value and a largest value of coordinates along the first direction in an image portion indicating the articular cavity region, as the width of the articular cavity region, a difference between a smallest value and a largest value of coordinates along the second direction in the image portion indicating the articular cavity region, and as the shape of the articular cavity region, an angle between a straight line joining a center of an interrupted portion of an image portion indicating a bone surface to one end of an image portion indicating an articular capsule and another straight line joining the center of the interrupted portion of the image portion to another end of the image portion indicating the articular capsule.

In this way, based on a feature point of an image indicating a detected articular cavity region, disease activity of the articular cavity region is quantified.

(20) Further, the ultrasound diagnostic device (18) pertaining to one aspect of the present invention may be configured such that the pathology analyzer quantifies at least one of a total area of a blood-flow signal in the image portion indicating the articular cavity region, a ratio of a total area of the blood-flow signal in the image portion indicating the articular cavity region to an area of the image portion indicating the articular cavity region, and a number of blood-flow signals as a continuous area in the image portion indicating the articular cavity region.

In this way, based on a blood-flow signal of the articular cavity region, disease activity of the articular cavity region is quantified.

(21) Further, the ultrasound diagnostic device (20) pertaining to one aspect of the present invention may be configured such that the pathology analyzer quantifies, in combination, a blood-flow signal position in the image portion indicating the articular cavity region and at least one of the total area of the blood-flow signal in the image portion indicating the articular cavity region, the ratio of the total area of the blood-flow signal in the image portion indicating the articular cavity region to the area of the image portion indicating the articular cavity region, and the number of blood-flow signals as the continuous area in the image portion indicating the articular cavity region.

In this way, based on a blood-flow signal and a position thereof, disease activity of the articular cavity region is quantified.

(22) Further, the ultrasound diagnostic device (2) pertaining to one aspect of the present invention may further include a pathology analyzer that performs quantification of disease activity in the synovial membrane by using the image portion indicating the synovial membrane specified by the component specifier.

In this way, quantification of disease activity is performed based on the state of the synovial membrane.

(23) Further, the ultrasound diagnostic device (22) pertaining to one aspect of the present invention may be configured such that the pathology analyzer performs quantification based on whether or not an image portion indicating the synovial membrane is intersected by a straight line joining image portions indicating metaphyses and whether or not the image portion indicating the synovial membrane extends to an image portion indicating a diaphysis.

In this way, quantification of disease activity is performed based on the range of the synovial membrane.

(24) Further, the ultrasound diagnostic device (22) pertaining to one aspect of the present invention may be configured such that the pathology analyzer quantifies at least one of a total area of a blood-flow signal in the image portion indicating the synovial membrane, a ratio of a total area of the blood-flow signal in the image portion indicating the synovial membrane to an area of the image portion indicating the synovial membrane, and a number of blood-flow signals as a continuous area in the image portion indicating the synovial membrane.

In this way, quantification of disease activity of the synovial membrane is performed based on a blood-flow signal of the synovial membrane.

(25) Further, the ultrasound diagnostic device (24) pertaining to one aspect of the present invention may be configured such that the pathology analyzer quantifies, in combination, a blood-flow signal position in the image portion indicating the synovial membrane and at least one of the total area of the blood-flow signal in the image portion indicating the synovial membrane, the ratio of the total area of the blood-flow signal in the image portion indicating the synovial membrane to the area of the image portion indicating the synovial membrane, and the number of blood-flow signals as the continuous area in the image portion indicating the synovial membrane.

In this way, quantification of disease activity of the synovial membrane is performed based on a blood-flow signal and a position thereof.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein

What is claimed is:

1. An ultrasound diagnostic device that specifies, from an ultrasound image of a subject that includes a joint, a joint image portion that indicates components of the joint, the ultrasound diagnostic device comprising:
   an image processing circuit that acquires the ultrasound image and specifies the joint image portion, including:
   an ultrasound image acquirer that acquires the ultrasound image; and
   a component specifier that specifies an image portion indicating a boundary between the components, wherein
   when a first direction is a depth direction substantially perpendicular to a surface of the subject, a second direction is a direction orthogonal to the first direction, a first pixel is a pixel at a pixel location N in the second direction, a second pixel is a pixel at a pixel location N+1 in the second direction, and N is a positive integer,
   the component specifier
   detects one or more feature lines from the ultrasound image by repeatedly, while incrementing N, linking the first pixel with the second pixel when luminance of the second pixel is high and the second pixel is in close proximity to the first pixel, and
   specifies which of the one or more feature lines indicates a boundary between components, based on an order in the first direction of the one or more feature lines.

2. The ultrasound diagnostic device of claim 1, wherein
   the component specifier specifies, from one of the one or more feature lines that is deep in the first direction, a bone surface as a boundary between the components, and further specifies, from a region in which the one or more feature lines are not detected that is less deep in the first direction than the bone surface, and based on a change of luminance in the first direction, an image portion indicating a synovial membrane.

3. The ultrasound diagnostic device of claim 1, wherein
   the first direction is parallel with a y axis and the second direction is parallel with an x axis,
   the first pixel is a pixel having a local maximum luminance relative to other pixels in the first direction, or a pixel linked with the first pixel in a previous iteration of the linking,
   the second pixel is a pixel among pixels having an x coordinate of N+1 that has a lowest Value according to Value=$m \cdot L(N+1,y) + n \cdot |y-y_N|$ where (N, $y_N$) are coordinates of the first pixel, L(N+1, y) is luminance of a given pixel having an x coordinate of N+1, (N+1, y) are coordinates of the given pixel, and m and n satisfy n>0>m.

4. The ultrasound diagnostic device of claim 3, wherein
   the image processing circuit further includes an edge enhancer, and the component specifier detects the one or more feature lines by the linking of the first pixel with the second pixel being performed based on a result of the edge enhancer performing edge enhancement on the ultrasound image.

5. The ultrasound diagnostic device of claim 1, wherein the component specifier detects a plurality of feature lines from the ultrasound image by repeatedly performing detection of one feature line from the ultrasound image, and detection of a new feature line is performed after eliminating a previously detected feature line from the ultrasound image.

6. The ultrasound diagnostic device of claim 1, wherein the component specifier, when specifying the image portion indicating the boundary between the components:
classifies a feature line that is shallow in the first direction as belonging to a skin segment, and classifies a feature line that is deep in the first direction as belonging to a bone segment; and
specifies an image portion indicating skin from the feature line classified as belonging to the skin segment, and an image portion indicating a bone surface from the feature line classified as belonging to the bone segment.

7. The ultrasound diagnostic device of claim 6, wherein the component specifier further specifies, as an image portion indicating an articular capsule, a feature line that is shallower in the first direction than the bone surface, both ends of the feature line being in close proximity to the bone surface.

8. The ultrasound diagnostic device of claim 6, wherein the component specifier further specifies, when the bone surface has an interrupted portion and the interrupted portion of the bone surface is deeper in the first direction than other portions of the bone surface, a center of the interrupted portion as indicating a center of a joint position in the second direction.

9. The ultrasound diagnostic device of claim 7, wherein the component specifier further specifies a region between the articular capsule and the bone surface as an image portion indicating an articular cavity region.

10. The ultrasound diagnostic device of claim 6, further comprising:
a pathology analyzer that performs quantification of disease activity in the bone surface by using the image portion indicating the bone surface specified by the component specifier.

11. The ultrasound diagnostic device of claim 10, wherein the pathology analyzer quantifies a smoothness of the bone surface.

12. The ultrasound diagnostic device of claim 11, wherein the pathology analyzer fits a predefined function to the image portion indicating the bone surface, and quantifies a difference between the image portion indicating the bone surface and the predefined function as the smoothness of the bone surface.

13. The ultrasound diagnostic device of claim 10, wherein the pathology analyzer quantifies bone erosion of the bone surface.

14. The ultrasound diagnostic device of claim 13, wherein the pathology analyzer calculates a first-order differential of the first direction or the second direction in the image portion indicating the bone surface, specifies an image portion indicating the bone erosion based on variation of the first-order differential, fits a predefined function to the image portion indicating the bone erosion, and quantifies a difference between the image portion indicating the bone erosion and the predefined function as a smoothness of the bone surface.

15. The ultrasound diagnostic device of claim 8, further comprising:
a pathology analyzer that performs quantification of disease activity in the joint by using the image portion indicating the bone surface specified by the component specifier, wherein
the pathology analyzer quantifies a straight-line length or a horizontal length of the interrupted portion of the bone surface.

16. The ultrasound diagnostic device of claim 7, further comprising:
a pathology analyzer that performs quantification of disease activity in the articular capsule by using the image portion indicating the articular capsule specified by the component specifier, wherein
the pathology analyzer quantifies at least one of a thickness, width, length, and area of the articular capsule.

17. The ultrasound diagnostic device of claim 16, wherein the pathology analyzer quantifies, as the thickness of the articular capsule, (i) a difference between a coordinate having a highest value in the first direction of an image portion indicating the articular capsule and a coordinate in the first direction of an end point of the image portion indicating the articular capsule, or (ii) a distance from the coordinate having the highest value in the first direction of the image portion indicating the articular capsule to a straight line connecting both ends of the image portion indicating the articular capsule,
as the width of the articular capsule, a coordinate difference along the second direction of coordinates at both ends of the image portion indicating the articular capsule,
as the length of the articular capsule, a length from one end of a feature line indicating the articular capsule to another end of the feature line, and
as the area of the articular capsule, an area surrounded by a straight line connecting both ends of the image portion indicating the articular capsule and the feature line indicating the articular capsule.

18. The ultrasound diagnostic device of claim 9, further comprising:
a pathology analyzer that performs quantification of disease activity in the articular cavity region by using the image portion indicating the articular cavity region specified by the component specifier, wherein
the pathology analyzer quantifies at least one of a height, width, area, and shape of the articular cavity region.

19. The ultrasound diagnostic device of claim 18, wherein the pathology analyzer quantifies, as the height of the articular cavity region, a difference between a smallest value and a largest value of coordinates along the first direction in an image portion indicating the articular cavity region,
as the width of the articular cavity region, a difference between a smallest value and a largest value of coordinates along the second direction in the image portion indicating the articular cavity region, and
as the shape of the articular cavity region, an angle between a straight line joining a center of an interrupted portion of an image portion indicating a bone surface to one end of an image portion indicating an articular capsule and another straight line joining the center of the interrupted portion of the image portion to another end of the image portion indicating the articular capsule.

20. The ultrasound diagnostic device of claim 18, wherein the pathology analyzer quantifies at least one of a total area of a blood-flow signal in the image portion indicating the articular cavity region, a ratio of a total area of the blood-flow signal in the image portion indicating the articular cavity region to an area of the image portion indicating the articular cavity region, and a number of blood-flow signals as a continuous area in the image portion indicating the articular cavity region.

21. The ultrasound diagnostic device of claim 20, wherein the pathology analyzer quantifies, in combination, a blood-flow signal position in the image portion indicating the articular cavity region and at least one of the total area of the blood-flow signal in the image portion indicating the articular cavity region, the ratio of the total area of the blood-flow signal in the image portion indicating the articular cavity region to the area of the image portion indicating the articular cavity region, and the number of blood-flow signals as the continuous area in the image portion indicating the articular cavity region.

22. The ultrasound diagnostic device of claim 2, further comprising:

a pathology analyzer that performs quantification of disease activity in the synovial membrane by using the image portion indicating the synovial membrane specified by the component specifier.

23. The ultrasound diagnostic device of claim 22, wherein the pathology analyzer performs quantification based on whether or not an image portion indicating the synovial membrane is intersected by a straight line joining image portions indicating metaphyses and whether or not the image portion indicating the synovial membrane extends to an image portion indicating a diaphysis.

24. The ultrasound diagnostic device of claim 22, wherein the pathology analyzer quantifies at least one of a total area of a blood-flow signal in the image portion indicating the synovial membrane, a ratio of a total area of the blood-flow signal in the image portion indicating the synovial membrane to an area of the image portion indicating the synovial membrane, and a number of blood-flow signals as a continuous area in the image portion indicating the synovial membrane.

25. The ultrasound diagnostic device of claim 24, wherein the pathology analyzer quantifies, in combination, a blood-flow signal position in the image portion indicating the synovial membrane and at least one of the total area of the blood-flow signal in the image portion indicating the synovial membrane, the ratio of the total area of the blood-flow signal in the image portion indicating the synovial membrane to the area of the image portion indicating the synovial membrane, and the number of blood-flow signals as the continuous area in the image portion indicating the synovial membrane.

* * * * *